(12) United States Patent
Wang et al.

(10) Patent No.: US 10,875,853 B2
(45) Date of Patent: Dec. 29, 2020

(54) (HETERO)ARYLAMIDE COMPOUND FOR INHIBITING PROTEIN KINASE ACTIVITY

(71) Applicant: Shenzhen TargetRx, Inc., Guangdong (CN)

(72) Inventors: Yihan Wang, Guangdong (CN); Jiuyang Zhao, Guangdong (CN); Yixin Ai, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 0 days.

(21) Appl. No.: 16/479,271

(22) PCT Filed: Jan. 19, 2018

(86) PCT No.: PCT/CN2018/073338
§ 371 (c)(1),
(2) Date: Jul. 19, 2019

(87) PCT Pub. No.: WO2018/133826
PCT Pub. Date: Jul. 26, 2018

(65) Prior Publication Data
US 2019/0375745 A1    Dec. 12, 2019

(30) Foreign Application Priority Data

Jan. 20, 2017 (CN) .......................... 2017 1 0044900

(51) Int. Cl.
*C07D 417/14* (2006.01)
*A61P 35/00* (2006.01)
*C07D 401/14* (2006.01)

(52) U.S. Cl.
CPC ............ *C07D 417/14* (2013.01); *A61P 35/00* (2018.01); *C07D 401/14* (2013.01)

(58) Field of Classification Search
CPC .................................................. C07D 417/14
USPC ....................................................... 546/271
See application file for complete search history.

(56) References Cited

U.S. PATENT DOCUMENTS

| 7,494,997 B2 | 2/2009 | Asaki et al. |
| 2015/0141427 A1 | 5/2015 | Furet et al. |
| 2018/0134695 A1 | 5/2018 | Furet et al. |

FOREIGN PATENT DOCUMENTS

| CN | 1678590 A | 10/2005 |
| CN | 103739595 A | 4/2014 |
| CN | 104302634 A | 1/2015 |
| CN | 104334529 A | 2/2015 |
| CN | 104379574 A | 2/2015 |
| JP | 2015-520157 A | 7/2015 |
| JP | 2015-520158 A | 7/2015 |
| WO | WO 2015/106292 A1 | 7/2015 |

OTHER PUBLICATIONS

King, Med. Chem. Principle and Practice (1994) pp. 206-208.*
International Search Report and Written Opinion for Application No. PCT/CN20108/073338, dated Apr. 17, 2018.
International Preliminary Report on Patentability for Application No. PCT/CN2018/073338, dated Aug. 1, 2019.
English Translation of Notice of Reasons for Refusal for Japanese Patent Application No. 2019-560439, dated May 26, 2020.

* cited by examiner

*Primary Examiner* — Taofiq A Solola
(74) *Attorney, Agent, or Firm* — Wolf, Greenfield & Sacks, P.C.

(57) ABSTRACT

Provided are a (hetero)arylamide compound as shown in formula (I) having an inhibitory effect on protein kinase activity, a pharmaceutically acceptable salt, a stereoisomer, a solvate or hydrate thereof, a pharmaceutical composition including the compound or a derivative thereof, and a method for preparing the compound. The compound can be used as an irreversible inhibitor for protein kinase, for preparing a plurality of drugs including an anti-tumour drug.

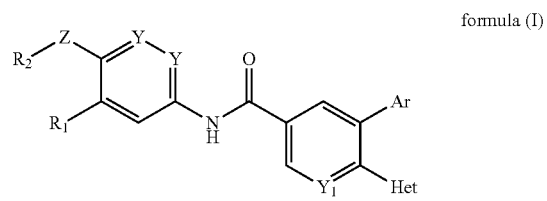

formula (I)

8 Claims, No Drawings

(HETERO)ARYLAMIDE COMPOUND FOR INHIBITING PROTEIN KINASE ACTIVITY

CROSS REFERENCE TO RELATED APPLICATIONS

The present application is a national application of PCT/CN2018/073338 filed on Jan. 19, 2018, which claims the priority of the Chinese Patent Application No. 201710044900.X filed on Jan. 20, 2017. The Chinese Patent Application No. 201710044900.X is incorporated herein by reference as part of the disclosure of the present application.

FIELD OF THE PRESENT DISCLOSURE

The present disclosure belongs to the pharmaceutical field. In particular, the present disclosure relates to (hetero)arylamide compounds which inhibit the tyrosine kinase activity of Abelson protein (Abl1), Abelson-related protein (Abl2) and related chimeric proteins, particularly Bcr-Abl1, relates to pharmaceutical compositions containing the same, and methods for their preparation and use thereof.

BACKGROUND OF THE PRESENT DISCLOSURE

Protein tyrosine kinases (PTKs) are a class of kinases that are involved in proteinases, which catalyze the transfer of γ-phosphate on ATP to protein tyrosine residues, and catalyze the phosphorylation of the phenolic hydroxyl groups on various protein tyrosine residues, thereby in turn activate functional proteins. Protein tyrosine kinases play an important role in the cellular signal transduction pathway, regulating a series of physiological and biochemical processes such as cell growth, differentiation and death. Abnormal expression of protein tyrosine kinase can lead to disturbances in cell proliferation regulation, which in turn leads to tumorigenesis. In addition, the abnormal expression of protein tyrosine kinase is also closely related to tumor invasion and metastasis, tumor angiogenesis, and chemotherapy resistance of tumors.

The tyrosine kinase expressed by the Bcr-Abl fusion gene can cause changes in cell proliferation, adhesion and survival properties, leading to the occurrence of various tumors. Inhibition of Bcr-Abl tyrosine kinase can effectively inhibit tumor growth.

ABL-001 (also known as Asciminib, chemical name (R)—N-(4-(chlorodifluoromethoxy)phenyl)-6-(3-hydroxypyrrolidin-1-yl)-5-(1H-pyrazol-5-yl)nicotinamide, which has the following structural formula) is an allosteric inhibitor of ABL1 kinase developed by Novartis Pharmaceuticals Co., Ltd., which inactivates ABL1 by targeting its myristoyl pocket, and is effective in preventing the emergence of drug resistance in the application of ATP inhibitors and/or allosteric inhibitors when used in combination with inhibitors of BCR-ABL tyrosine kinase that compete with ATP. ABL-001 has been shown to be effective in eradicating CML in a mouse model when combined with the second-generation BCR-ABL inhibitor nilotinib (Andrew A. Wylie et al. (2017) Nature 543, 733-737). Novartis is developing a clinical treatment regimen of ABL-001 in combination with various ATP-competitive BCR-ABL inhibitors, including imatinib, nilotinib, and dasatinib.

ABL-001

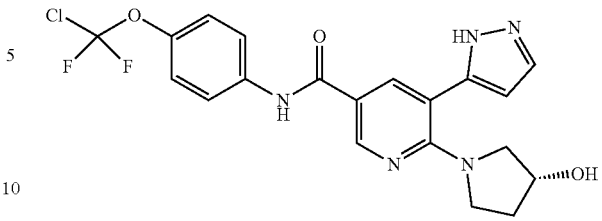

Therefore, it is necessary to further develop novel Bcr-Abl inhibitors.

SUMMARY OF THE PRESENT DISCLOSURE

The present disclosure provides a novel (hetero)arylamide compound and a composition comprising the same and use thereof, which have better Bcr-Abl kinase inhibitory activity (especially for T315I mutation), lower side effects and/or better pharmacodynamics/pharmacokinetic properties, and thus can be used to treat diseases mediated by Bcr-Abl kinase.

In this regard, the technical solution adopted by the present disclosure is as follows:

In the first aspect, the present disclosure provides a (hetero)arylamide compound represented by formula (I), or a pharmaceutically acceptable salt, a stereoisomer, a solvate or a hydrate thereof:

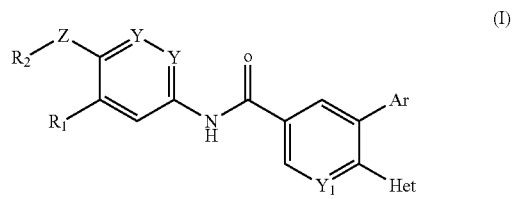

(I)

wherein:

$Y_1$ is selected from $CR_a$ or N;

Y is independently selected from $CR_a$ or N;

$R_1$ is selected from hydrogen, halo, nitrile, nitro, $C_{1-6}$ alkyl or $C_{1-6}$ haloalkyl, wherein the said $C_{1-6}$ alkyl or $C_{1-6}$ haloalkyl is optionally substituted by $R_{1a}$ group;

$R_2$ is selected from hydrogen, $C_{1-6}$ alkyl or $C_{1-6}$ haloalkyl, wherein the said $C_{1-6}$ alkyl or $C_{1-6}$ haloalkyl is optionally substituted by $R_{2a}$ group;

Z is a chemical bond, O, $S(O)_{0-2}$ or $NR_b$;

or —Z—$R_2$ together form —$SF_5$;

Ar is

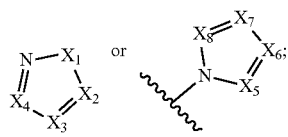

wherein $X_1$ is selected from O, S or $NR_b$, $X_2$ to $X_8$ are independently selected from CR or N;

and when $X_1$ is O or S, one of $X_2$, $X_3$ and $X_4$ is C atom that connects the parent core; when $X_1$ is $NR_b$, one of $X_2$, $X_3$ and $X_4$ is C atom that connects the parent core and wherein at least one of them is N;

Het is

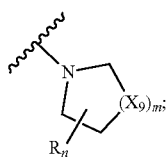

wherein $X_9$ is selected from O, S, $NR_b$ or $C(R)_2$;

m is 0, 1 or 2;

n is 0, 1, 2, 3, 4, 5 or 6;

$R_a$ is independently selected from hydrogen, halo, nitrile, nitro, hydroxy, —$NH_2$, —$NHC_{1-6}$ alkyl, —$N(C_{1-6}$ alkyl$)_2$, $C_{1-6}$ alkyl, $C_{1-6}$ haloalkyl or $C_{1-6}$ alkoxyl;

$R_b$ is independently selected from hydrogen, $C_{1-6}$ alkyl or $C_{1-6}$ haloalkyl;

$R_{1a}$, $R_{2a}$ and R are independently selected from hydrogen, halo, hydroxy, —$NH_2$, —$NHC_{1-6}$ alkyl, —$N(C_{1-6}$ alkyl$)_2$, $C_{1-6}$ alkyl, $C_{1-6}$ haloalkyl, $C_{1-6}$ alkoxyl, $C_{3-7}$ cycloalkyl, $C_{3-7}$ heterocyclyl, $C_{6-10}$ aryl or $C_{5-10}$ heteroaryl;

or two R groups on the same or adjacent atoms may together form $C_{3-7}$ cycloalkyl, $C_{3-7}$ heterocyclyl, $C_{6-10}$ aryl or $C_{5-10}$ heteroaryl.

In another aspect, the disclosure provides a pharmaceutical composition comprising a compound disclosed herein and a pharmaceutically acceptable excipient. In a particular embodiment, the compound disclosed herein is provided in the pharmaceutical composition in an effective amount. In a particular embodiment, the compound disclosed herein is provided in a therapeutically effective amount. In a particular embodiment, the compound disclosed herein is provided in a prophylactically effective amount.

In another aspect, the disclosure provides a pharmaceutical composition comprising a compound disclosed herein and a pharmaceutically acceptable excipient.

In another aspect, the disclosure provides a kit containing a compound disclosed herein and other therapeutic agents, and pharmaceutically acceptable carriers, adjuvants or vehicles.

In another aspect, the disclosure provides the use of a compound disclosed herein in the manufacture of a medicament for the treatment and/or prevention of diseases caused by Bcr-Abl.

In another aspect, the disclosure provides a method of treating and/or preventing diseases caused by Bcr-Abl in a subject, comprising administering to the subject a compound disclosed herein or a composition disclosed herein.

In another aspect, the disclosure provides a compound disclosed herein or a composition disclosed herein, for use in the treatment and/or prevention of diseases caused by Bcr-Abl.

In a specific embodiment, the disease may be selected from the group consisting of: solid tumor, sarcoma, acute lymphocytic leukemia, acute myeloid leukemia, chronic lymphocytic leukemia, chronic myeloid leukemia, gastrointestinal stromal tumor, thyroid cancer, gastric cancer, rectal cancer, multiple myeloma, neoplasia, and other proliferative disease or proliferative diseases.

In a specific embodiment, the Bcr-Abl caused disease is chronic myeloid leukemia, gastrointestinal stromal tumor, acute myeloid leukemia, thyroid cancer, metastatic invasive cancer, or a combination thereof.

In another aspect, the compounds disclosed herein also have the potential to treat or prevent diseases or disorders associated with abnormally activated kinase activity of wild-type Abl, including non-malignant diseases or disorders, such as CNS diseases in particular neurodegenerative diseases (for example Alzheimer's, Parkinson's diseases), motoneuroneuron diseases (amyotophic lateral sclerosis), muscular dystrophies, autoimmune and inflammatory diseases (diabetes and pulmonary fibrosis), viral infections, and prion diseases.

In a specific embodiment, the compound is administered orally, subcutaneously, intravenously or intramuscularly. In a specific embodiment, the compound is administered chronically.

Other objects and advantages of the present disclosure will be apparent to those skilled in the art from the following specific embodiments, examples and claims.

Definitions

Chemical Definitions

Definitions of specific functional groups and chemical terms are described in more detail below.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

It should be understood that when described herein any of the moieties defined forth below may be substituted with a variety of substituents, and that the respective definitions are intended to include such substituted moieties within their scope as set out below. Unless otherwise stated, the term "substituted" is to be defined as set out below.

"$C_{1-6}$ alkyl" refers to a radical of a straight-chain or branched saturated hydrocarbon group having from 1 to 6 carbon atoms, and it is also referred to herein as "lower alkyl". In some embodiments, $C_{1-4}$ alkyl is particularly preferred. Examples of alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-6}$ alkyl (e.g., —$CH_3$). In certain embodiments, the alkyl group is substituted $C_{1-6}$ alkyl.

"$C_{1-6}$ alkoxy" refers to the group —OR wherein R is a substituted or unsubstituted $C_{1-6}$ alkyl group. In some embodiments, $C_{1-4}$ alkoxy group is particularly preferred. Specific alkoxy groups include, but are not limited to, methoxy, ethoxy, n-propoxy, isopropoxy, n-butoxy, tert-butoxy, sec-butoxy, n-pentyloxy, n-hexyloxy and 1,2-dimethylbutoxy.

"Halo" or "halogen" means fluorine (F), chlorine (Cl), bromine (Br) and iodine (I). In some embodiments, the halo group is F, —Cl or Br. In some embodiments, the halogen group is Cl. In some embodiments, the halogen group is F. In some embodiments, the halogen group is Br.

Thus, "$C_{1-6}$ haloalkyl" refers to the above "$C_{1-6}$ alkyl", which is substituted by one or more halo groups. In some embodiments, $C_{1-4}$ haloalkyl group is particularly preferred, and more preferably $C_{1-2}$ haloalkyl group. Exemplary haloalkyl groups include, but are not limited to, —$CF_3$, —$CH_2F$, —$CHF_2$, —$CClF_2$, —$CHFCH_2F$, —$CH_2CHF_2$, —CF$_2$CF$_3$, —CF$_2$CClF$_2$, —CF$_2$CH$_3$, —CCl$_3$, —CH$_2$Cl, —CHCl$_2$, 2,2,2-trifluoro-1,1-dimethyl-ethyl, and the like.

"C$_{3-7}$ cycloalkyl" refers to a radical of a non-aromatic cyclic hydrocarbon group having from 3 to 7 ring carbon atoms and zero heteroatoms. In some embodiments, C$_{3-6}$ cycloalkyl is especially preferred, and C$_{5-6}$ cycloalkyl is more preferred. Cycloalkyl also includes ring systems wherein the cycloalkyl ring, as defined above, is fused with one or more aryl or heteroaryl groups wherein the point of attachment is on the cycloalkyl ring, and in such instances, the number of carbons continue to designate the number of carbons in the cycloalkyl ring system. Exemplary cycloalkyl groups include, but is not limited to, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), cycloheptyl (C$_7$), cycloheptenyl (C$_7$), cycloheptadienyl (C$_7$), cycloheptatrienyl (C$_7$), and the like. Unless otherwise specified, each instance of a cycloalkyl group is independently optionally substituted, i.e., unsubstituted (an "unsubstituted cycloalkyl") or substituted (a "substituted cycloalkyl") with one or more substituents. In certain embodiments, the cycloalkyl group is unsubstituted C$_{3-7}$ cycloalkyl. In certain embodiments, the cycloalkyl group is a substituted C$_{3-7}$ cycloalkyl.

"C$_{3-7}$ heterocyclyl" refers to a radical of a 3- to 7-membered non-aromatic ring system having ring carbon atoms and 1 to 4 ring heteroatoms, wherein each heteroatom is independently selected from nitrogen, oxygen, sulfur, boron, phosphorus, and silicon. In heterocyclyl groups that contain one or more nitrogen atoms, the point of attachment can be a carbon or nitrogen atom, as valency permits. In some embodiments, C$_{3-6}$ heterocyclyl is especially preferred, which is a radical of a 3- to 6-membered non-aromatic ring system having ring carbon atoms and 1 to 3 ring heteroatoms. In some embodiments, C$_{5-6}$ heterocyclyl is more preferred, which is a radical of a 5- to 6-membered non-aromatic ring system having ring carbon atoms and 1 to 3 ring heteroatoms. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted C$_{3-7}$ heterocyclyl. In certain embodiments, the heterocyclyl group is substituted C$_{3-7}$ heterocyclyl. Heterocyclyl also includes ring systems wherein the heterocyclyl ring, as defined above, is fused with one or more cycloalkyl groups, wherein the point of attachment is on the cycloalkyl ring; or wherein the heterocyclyl ring, as defined above, is fused with one or more aryl or heteroaryl groups, wherein the point of attachment is on the heterocyclyl ring; and in such instances, the number of ring members continue to designate the number of ring members in the heterocyclyl ring system. Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 5-membered heterocyclyl groups fused to a C$_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"C$_{6-10}$ aryl" refers to a radical of a monocyclic or polycyclic (e.g., bicyclic) 4n+2 aromatic ring system (e.g., having 6, 10 π electrons shared in a cyclic array) having 6-10 ring carbon atoms and zero heteroatoms. In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). Aryl also includes ring systems wherein the aryl ring, as defined above, is fused with one or more cycloalkyl, or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-10}$ aryl. In certain embodiments, the aryl group is substituted C$_{6-10}$ aryl.

"C$_{5-10}$ heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms, wherein each heteroatom is independently selected from nitrogen, oxygen and sulfur. In heteroaryl groups that contain one or more nitrogen atoms, the point of attachment can be a carbon or nitrogen atom, as valency permits. Heteroaryl bicyclic ring systems can include one or more heteroatoms in one or both rings. Heteroaryl further includes ring systems wherein the heteroaryl ring, as defined above, is fused with one or more cycloalkyl, or heterocyclyl groups wherein the point of attachment is on the heteroaryl ring, and in such instances, the number of ring members continue to designate the number of ring members in the heteroaryl ring system. In some embodiments, C$_{5-6}$ heteroaryl is especially preferred, which is a radical of a 5-6 membered monocyclic or bicyclic 4n+2 aromatic ring system having ring carbon atoms and 1-4 ring heteroatoms. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5- to 10-membered heteroaryl. In certain embodiments, the heteroaryl group is substituted 5- to 10-membered heteroaryl. Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl.

Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Nitrile group" represents the group —CN.
"Nitro group" represents the group —NO$_2$.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present disclosure include those derived from suitable inorganic and organic acids and bases.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound disclosed herein may vary depending on such factors as the desired biological endpoint, the pharmacokinetics of the compound, the disease being treated, the mode of administration, and the age, health, and condition of the subject. An effective amount encompasses therapeutically effective amount and prophylactically effective amount.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

"Bcr-Abl1" refers to a fusion protein created from the N-terminal exons of the breakpoint cluster region (BCR) gene and the major C-terminal part (exons 2-11) of the Abelson (ABL1) gene. The most common fusion transcripts encode for a 210-kDa protein (p210 Bcr-Abl1), while rarer tanscripts encode a 190-kDa protein (p190 Bcr-Abl1) and a 230-kDa protein (p230 Bcr-Abl1). The Abl1 sequences of these proteins contains an Abl1 tyrosine kinase domain which is tightly regulated in the wild-type protein, but constitutively activated in the Bcr-Abl1 fusion proteins. This deregulated tyrosine kinase interacts with multiple cellular signalling pathways leading to transformation and deregulated proliferation of the cells.

"Bcr-Abl1 mutants" refers to the numerous single site mutations in Bcr-Abl1 including: Glu255→Lys, Glu255→Val, Thr315→Ile, Met244→Val, Phe317→Leu, Leu248→Val, Met343→Thr, Gly250→Ala, Met351→Thr, Gly250→Glu, Glu355→Gly, Gln252→His, Phe358→Ala, Gln252→Arg, Phe359→Val, Tyr253→His, Val379→Ile, Tyr253→Phe, Phe382→Leu, Glu255→Lys, Leu387→Met, Glu255→Val, His396→Pro, Phe311→Ile, His396→Arg, Phe311→Leu, Ser417→Tyr, Thr315→Ile, Glu459→Lys and Phe486→Ser.

"C-Abl" refers to the full length gene product of a non-mutated wild-type Abl1.

DETAILED DESCRIPTION OF THE EMBODIMENTS

Compound

In the present disclosure, "compound disclosed herein" refers to the following compound of formula (I), (Ia) and (Ib), or a pharmaceutically acceptable salt, a stereoisomer, a solvate, or a hydrate thereof.

In one embodiment, the present disclosure relates to a compound of formula (I), or a pharmaceutically acceptable salt, a stereoisomer, a solvate or a hydrate thereof:

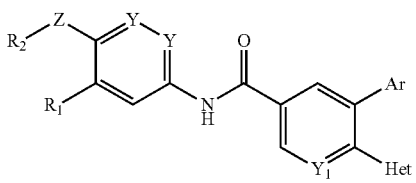

(I)

wherein:

Y$_1$ is selected from CR$_a$ or N;

Y is independently selected from CR$_a$ or N;

R$_1$ is selected from hydrogen, halo, nitrile, nitro, C$_{1-6}$ alkyl or C$_{1-6}$ haloalkyl, wherein the said C$_{1-6}$ alkyl or C$_{1-6}$ haloalkyl is optionally substituted by R$_{1a}$ group;

R$_2$ is selected from hydrogen, C$_{1-6}$ alkyl or C$_{1-6}$ haloalkyl, wherein the said C$_{1-6}$ alkyl or C$_{1-6}$ haloalkyl is optionally substituted by R$_{2a}$ group;

Z is a chemical bond, O, S(O)$_{0-2}$ or NR$_b$;

or —Z—R$_2$ together form —SF$_5$;

Ar is

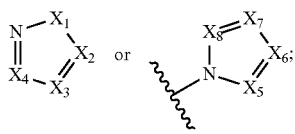

wherein X$_1$ is selected from O, S or NR$_b$, X$_2$ to X$_8$ are independently selected from CR or N;

and when X$_1$ is O or S, one of X$_2$, X$_3$ and X$_4$ is C atom that connects the parent core; when X$_1$ is NR$_b$, one of X$_2$, X$_3$ and X$_4$ is C atom that connects the parent core and wherein at least one of them is N;

Het is

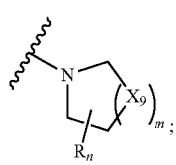

wherein X$_9$ is selected from O, S, NR$_b$ or C(R)$_2$;

m is 0, 1 or 2;

n is 0, 1, 2, 3, 4, 5 or 6;

R$_a$ is independently selected from hydrogen, halo, nitrile, nitro, hydroxy, —NH$_2$, —NHC$_{1-6}$ alkyl, —N(C$_{1-6}$ alkyl)$_2$, C$_{1-6}$ alkyl, C$_{1-6}$ haloalkyl or C$_{1-6}$ alkoxyl;

R$_b$ is independently selected from hydrogen, C$_{1-6}$ alkyl or C$_{1-6}$ haloalkyl;

R$_{1a}$, R$_{2a}$ and R are independently selected from hydrogen, halo, hydroxy, —NH$_2$, —NHC$_{1-6}$ alkyl, —N(C$_{1-6}$ alkyl)$_2$, C$_{1-6}$ alkyl, C$_{1-6}$ haloalkyl, C$_{1-6}$ alkoxyl, C$_{3-7}$ cycloalkyl, C$_{3-7}$ heterocyclyl, C$_{6-10}$ aryl or C$_{5-10}$ heteroaryl;

or two R groups on the same or adjacent atoms may together form C$_{3-7}$ cycloalkyl, C$_{3-7}$ heterocyclyl, C$_{6-10}$ aryl or C$_{5-10}$ heteroaryl.

In another embodiment, the present disclosure relates to the above compound, wherein Ar is

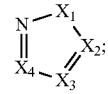

wherein X$_1$ is S, X$_2$ to X$_4$ are independently selected from CR or N; and one of X$_2$, X$_3$ and X$_4$ is C atom that connects the parent core;

or, Ar is selected from the following groups that are optionally substituted by one or two R:

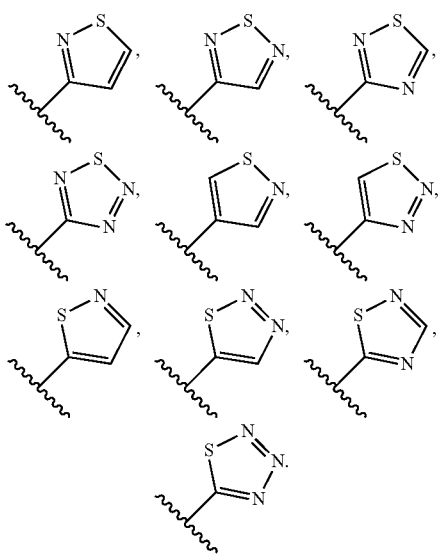

In another embodiment, the present disclosure relates to the above compound, which is formula (Ia), or a pharmaceutically acceptable salt, a stereoisomer, a solvate or a hydrate thereof:

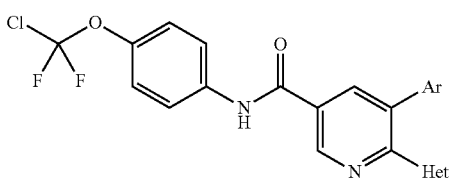

(Ia)

wherein, Ar and Het are as defined herein.

In another embodiment, the present disclosure relates to the above compound, or a pharmaceutically acceptable salt, a stereoisomer, a solvate or a hydrate thereof, wherein:

Ar is

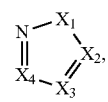

wherein, X$_1$ to X$_4$ are as defined herein;

or, Ar is selected from the following groups that are optionally substituted by one or two R:

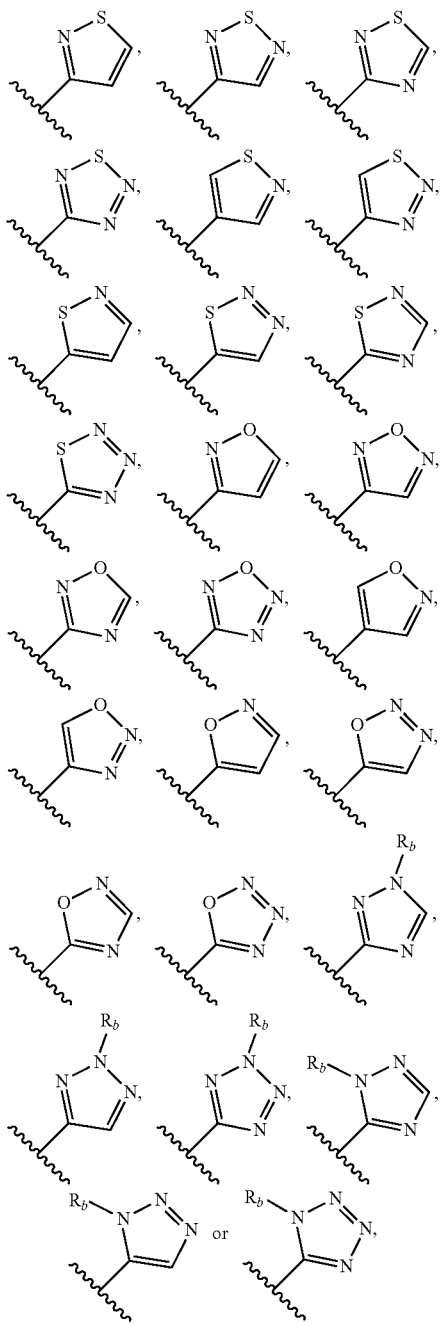

wherein, R and $R_b$ are as defined herein.

In another embodiment, the present disclosure relates to the above compound, or a pharmaceutically acceptable salt, a stereoisomer, a solvate or a hydrate thereof, wherein:

Ar is

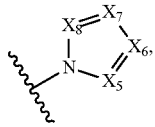

wherein, $X_5$ to $X_8$ are as defined herein;

or, Ar is selected from the following groups that are optionally substituted by R:

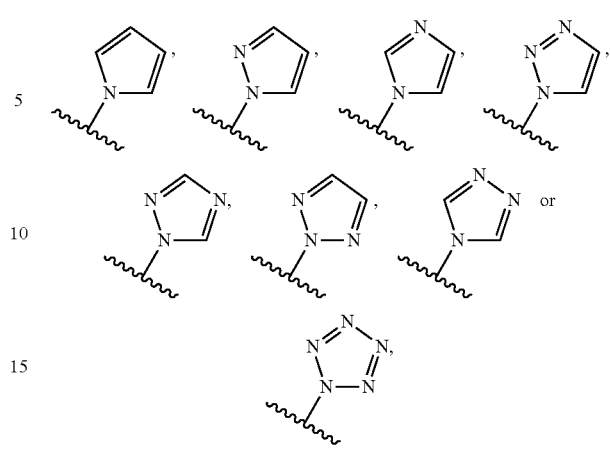

wherein, R is as defined herein.

In another embodiment, the present disclosure relates to the above compound, or a pharmaceutically acceptable salt, a stereoisomer, a solvate or a hydrate thereof, wherein:

Het is

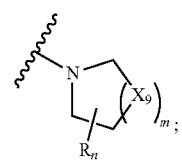

wherein, $X_9$ is $C(R)_2$, and m, n and R are as defined herein;

or, Het is selected from the following groups that are optionally substituted by one, two, three or more R:

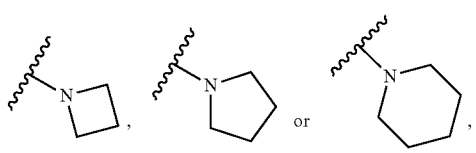

wherein R is as defined herein;

or, Het is selected from the following groups:

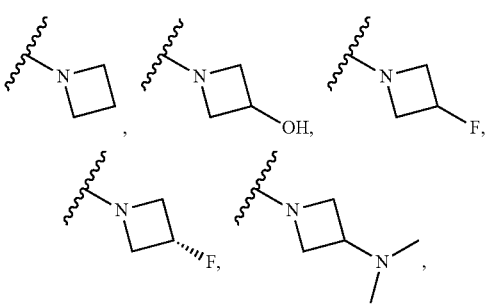

-continued

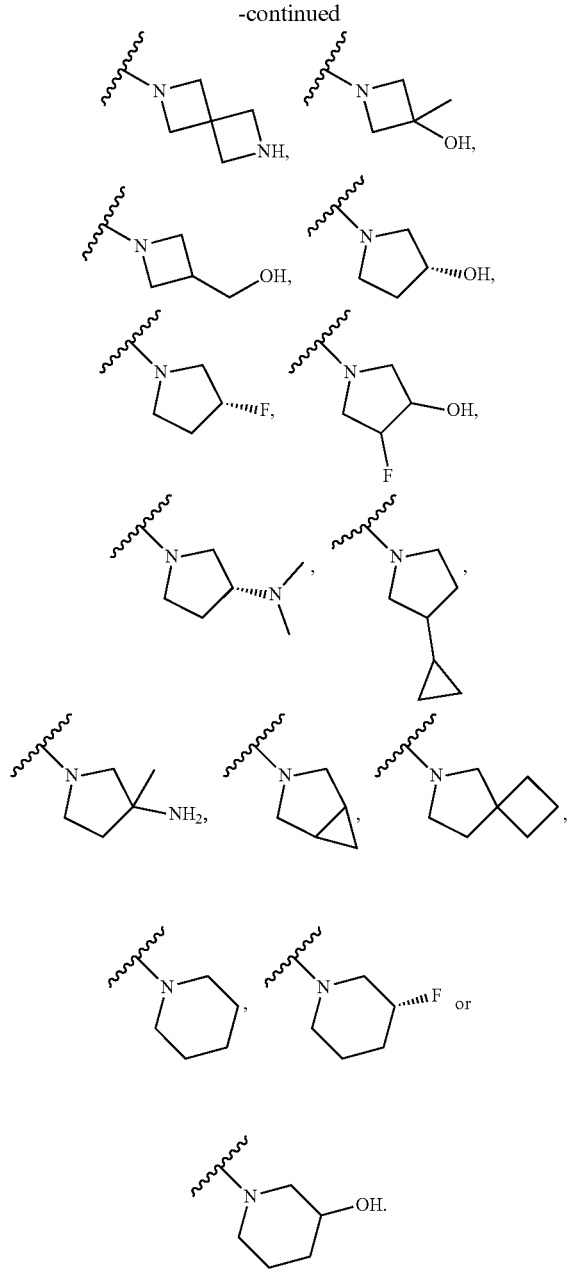

In another embodiment, the present disclosure relates to the above compound, or a pharmaceutically acceptable salt, a stereoisomer, a solvate or a hydrate thereof, wherein:
Het is

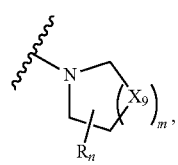

wherein, one $X_9$ is selected from O, S or $NR_b$, and the optionally present other $X_9$ is $C(R)_2$, and m, n, R and $R_b$ are as defined herein;

or, Het is selected from the following groups:

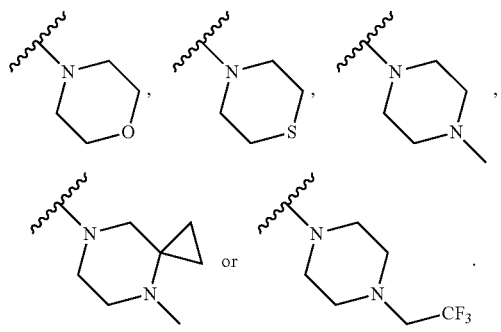

In another embodiment, the present disclosure relates to the above compound, which is formula (Ib), or a pharmaceutically acceptable salt, a stereoisomer, a solvate or a hydrate thereof:

(Ib)

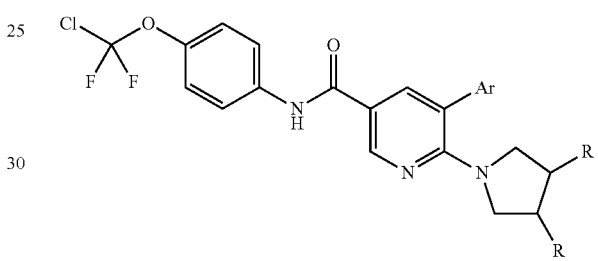

wherein:
Ar is

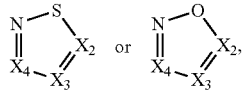

wherein $X_2$ to $X_4$ are independently selected from CR or N, and one of $X_2$, $X_3$ and $X_4$ is C atom that connects the parent core;
or, Ar is selected from the following groups that are optionally substituted by one or two R:

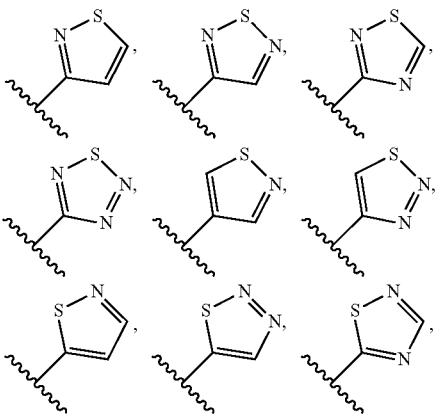

-continued

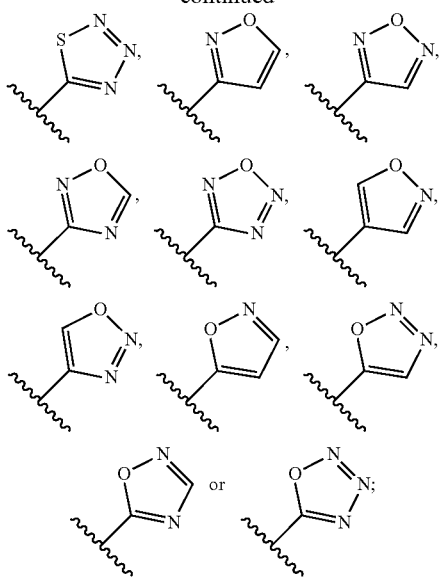

R is selected from hydrogen, halo, hydroxy, —NH$_2$, —NHC$_{1-6}$ alkyl, —N(C$_{1-6}$ alkyl)$_2$.

In another embodiment, the present disclosure relates to the above compound, which is formula (Ib), or a pharmaceutically acceptable salt, a stereoisomer, a solvate or a hydrate thereof:

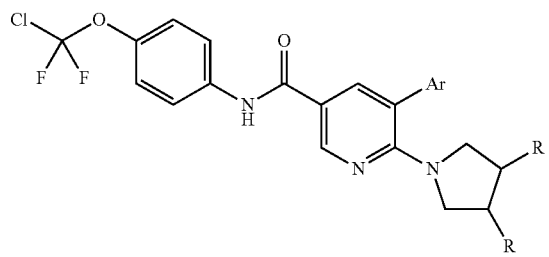

(Ib)

wherein:

Ar is selected from the following groups that are optionally substituted by one or two R:

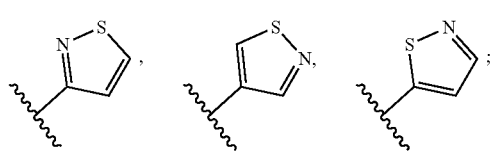

R is selected from hydrogen, halo, hydroxy, —NH$_2$, —NHC$_{1-6}$ alkyl, —N(C$_{1-6}$ alkyl)$_2$.

In another embodiment, the present disclosure relates to the above compound, which is formula (Ib), or a pharmaceutically acceptable salt, a stereoisomer, a solvate or a hydrate thereof:

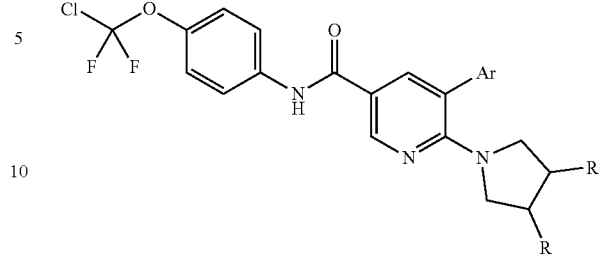

(Ib)

wherein:

Ar is selected from the following groups that are optionally substituted by one or two R:

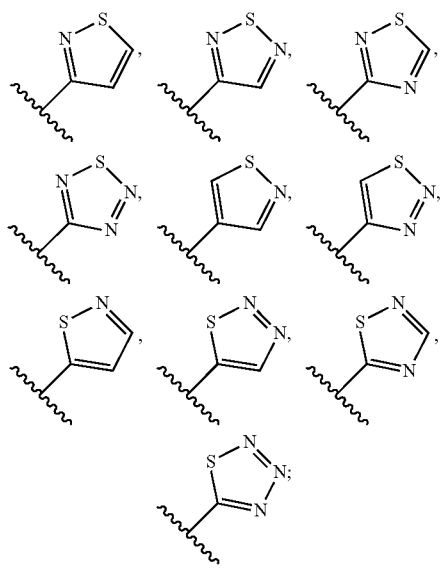

R is selected from hydrogen, hydroxyl.

In another embodiment, the present disclosure relates to the above compound, which is formula (Ib), or a pharmaceutically acceptable salt, a stereoisomer, a solvate or a hydrate thereof:

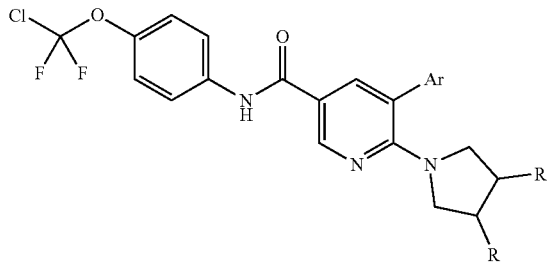

(Ib)

wherein:

Ar is selected from the following groups that are optionally substituted by one or two R:

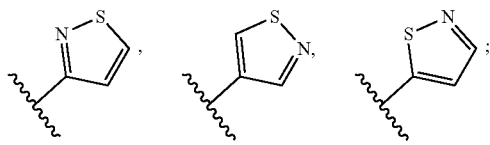 [SMILES: *c1ccsn1 ; *c1cnsc1 ; *c1ccns1]

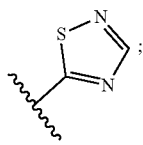

R is selected from hydrogen, halo, hydroxyl.

In another embodiment, the present disclosure relates to the above compound, which is formula (Ib), or a pharmaceutically acceptable salt, a stereoisomer, a solvate or a hydrate thereof:

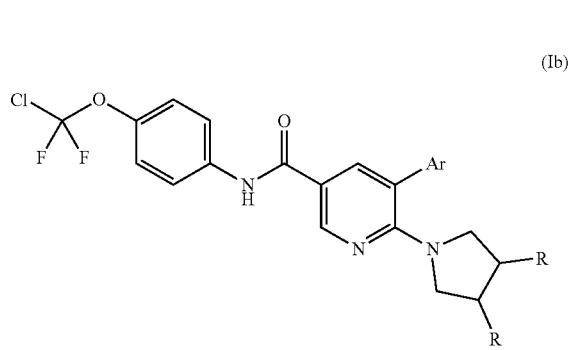

(Ib)

wherein:

Ar is selected from the following groups that are optionally substituted by one or two R:

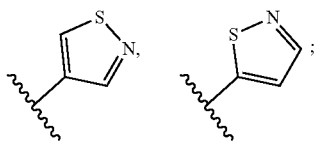 [SMILES: *c1cnsc1 ; *c1ccns1]

R is selected from hydrogen, hydroxyl.

In another embodiment, the present disclosure relates to the above compound, which is formula (Ib), or a pharmaceutically acceptable salt, a stereoisomer, a solvate or a hydrate thereof:

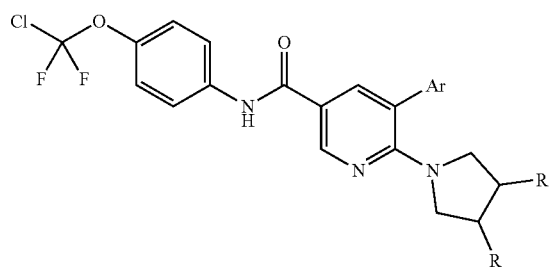

(Ib)

wherein:

Ar is selected from the following groups that are optionally substituted by one or two R:

R is selected from hydrogen, halo, hydroxyl.

In another embodiment, the present disclosure relates to the above compound, which is formula (Ib), or a pharmaceutically acceptable salt, a stereoisomer, a solvate or a hydrate thereof, wherein:

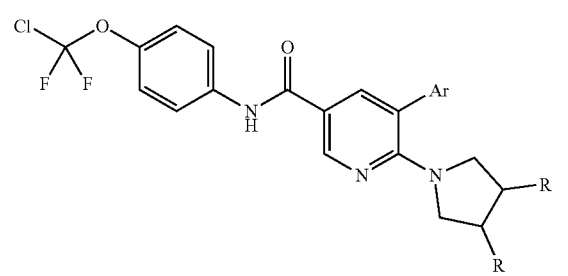

(Ib)

wherein:

Ar is

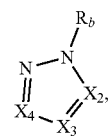

wherein $X_2$ to $X_4$ are independently selected from CR or N, and one of $X_2$, $X_3$ and $X_4$ is C atom that connects the parent core and wherein at least one of them is N;

or, Ar is selected from the following groups that are optionally substituted by one R:

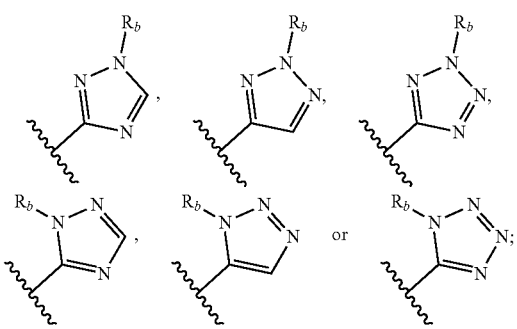

$R_6$ is selected from hydrogen, $C_{1-6}$ alkyl or $C_{1-6}$ haloalkyl;

R is selected from hydrogen, halo, hydroxy, —$NH_2$, —$NHC_{1-6}$ alkyl, —$N(C_{1-6}$ alkyl$)_2$.

In another embodiment, the present disclosure relates to the above compound, which is formula (Ic), or a pharmaceutically acceptable salt, a stereoisomer, a solvate or a hydrate thereof, wherein:

(Ic)

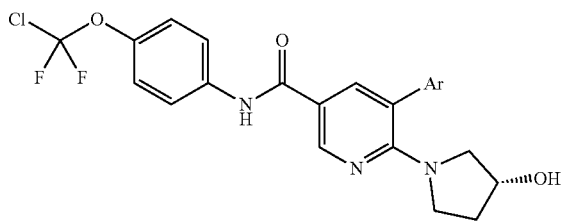

wherein:

Ar is selected from the following groups that are optionally substituted by one or two R:

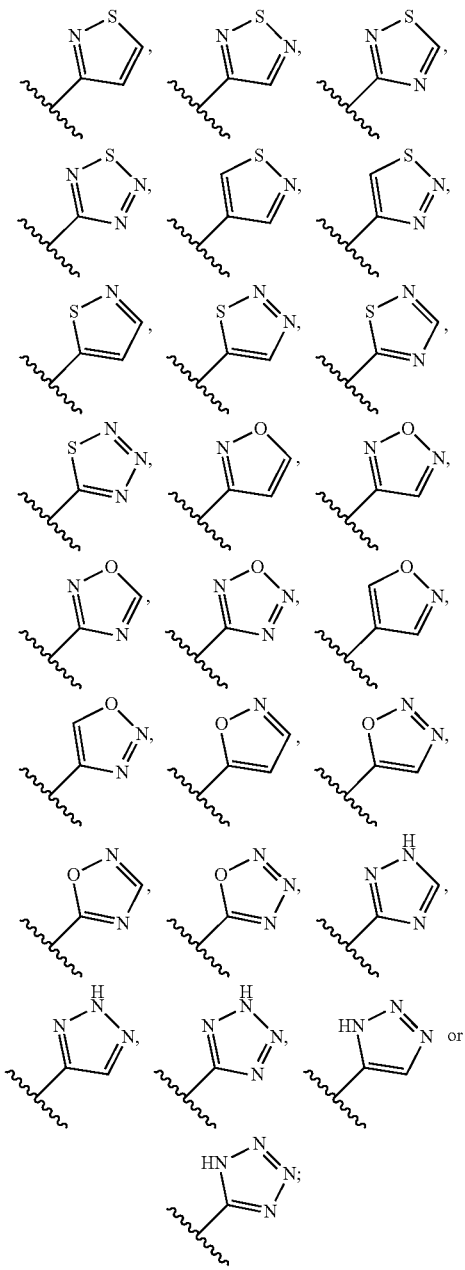

R is selected from hydrogen, halo, hydroxy, —NH$_2$, —NHC$_{1-6}$ alkyl, —N(C$_{1-6}$ alkyl)$_2$.

In another embodiment, the present disclosure relates to the above compound, which is formula (Ic), or a pharmaceutically acceptable salt, a stereoisomer, a solvate or a hydrate thereof, wherein:

(Ic)

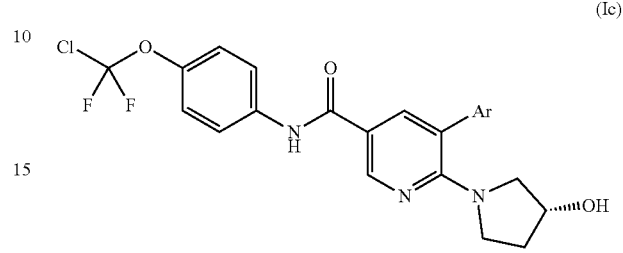

wherein:
Ar is selected from the following groups:

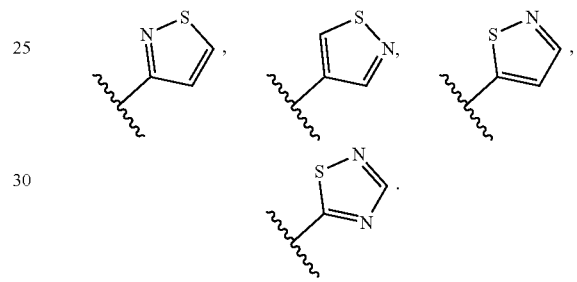

In another embodiment, the present disclosure relates to the above compound, which is formula (Ic), or a pharmaceutically acceptable salt, a stereoisomer, a solvate or a hydrate thereof, wherein:

(Ic)

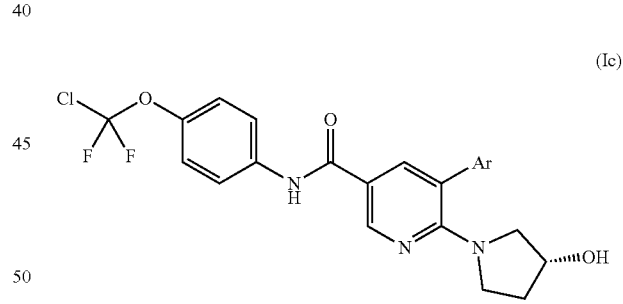

wherein:
Ar is selected from the following groups:

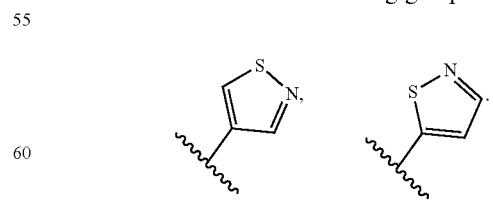

Y$_1$ and Y

In one specific embodiment, Y$_1$ is N; in another specific embodiment, Y$_1$ is CR$_a$; in another specific embodiment, Y$_1$ is CH.

In one specific embodiment, Y is $CR_a$; in another specific embodiment, Y is N; in another specific embodiment, Y is CH.

$R_1$

In one specific embodiment, $R_1$ is selected from hydrogen, halo, nitrile, nitro, $C_{1-6}$ alkyl or $C_{1-6}$ haloalkyl; in another specific embodiment, $R_1$ is selected from hydrogen, halo, nitrile, nitro or $C_{1-6}$ alkyl; in another specific embodiment, $R_1$ is selected from hydrogen or halo; in another specific embodiment, $R_1$ is hydrogen; in another specific embodiment, $R_1$ is halo (F, Cl, Br or I); in another specific embodiment, $R_1$ is nitrile; in another specific embodiment, $R_1$ is nitro; in another specific embodiment, $R_1$ is $C_{1-6}$ alkyl (methyl, ethyl, propyl, isopropyl, butyl, iso-butyl, tert-butyl, pentyl, iso-pentyl, hexyl, and the like); in another specific embodiment, $R_1$ is $C_{1-6}$ haloalkyl (—$CF_3$, —$CH_2F$, —$CHF_2$, —$CClF_2$, —$CHFCH_2F$, —$CH_2CHF_2$, —$CF_2CF_3$, —$CF_2CClF_2$, —$CF_2CH_3$, —$CCl_3$, —$CH_2Cl$, —$CHCl_2$, 2,2,2-trifluoro-1,1-dimethyl-ethyl, and the like).

$R_2$ and Z

In one specific embodiment, $R_2$ is selected from hydrogen, $C_{1-6}$ alkyl or $C_{1-6}$ haloalkyl; in another specific embodiment, $R_2$ is selected from $C_{1-6}$ alkyl or $C_{1-6}$ haloalkyl; in another specific embodiment, $R_2$ is hydrogen; in another specific embodiment, $R_2$ is $C_{1-6}$ alkyl (methyl, ethyl, propyl, isopropyl, butyl, iso-butyl, tert-butyl, pentyl, iso-pentyl, hexyl, and the like); in another specific embodiment, $R_2$ is $C_{1-6}$ haloalkyl (—$CF_3$, —$CH_2F$, —$CHF_2$, —$CClF_2$, —$CHFCH_2F$, —$CH_2CHF_2$, —$CF_2CF_3$, —$CF_2CClF_2$, —$CF_2CH_3$, —$CCl_3$, —$CH_2Cl$, —$CHCl_2$, 2,2,2-trifluoro-1,1-dimethyl-ethyl, and the like).

In one specific embodiment, Z is a chemical bond; in another specific embodiment, Z is O; in another specific embodiment, Z is $S(O)_{0-2}$; in another specific embodiment, Z is $NR_b$; in another specific embodiment, Z is NH.

In one specific embodiment, —Z—$R_2$ together form —$SF_5$.

Ar and $X_1$ to $X_8$

In one specific embodiment, Ar is

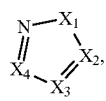

wherein $X_1$ is O or S; in more specific embodiment, Ar is

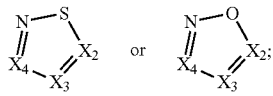

in more specific embodiment, Ar is

In the above specific embodiment regarding Ar, $X_2$ is CR; in another specific embodiment, $X_2$ is CH; in another specific embodiment, $X_2$ is N. In the above embodiment regarding Ar, $X_3$ is CR; in another specific embodiment, $X_3$ is CH; in another specific embodiment, $X_3$ is N. In the above specific embodiment regarding Ar, $X_4$ is CR; in another specific embodiment, $X_4$ is CH; in another specific embodiment, $X_4$ is N.

In the above mentioned embodiment, one of $X_2$, $X_3$ and $X_4$ is C atom that connects the parent core; in one specific embodiment, $X_2$ is C atom that connects the parent core; in another specific embodiment, $X_3$ is C atom that connects the parent core; in another specific embodiment, $X_4$ is C atom that connects the parent core.

In more specific embodiment, Ar is

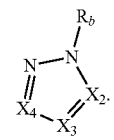

In the above specific embodiment regarding Ar, $X_2$ is CR; in another specific embodiment, $X_2$ is CH; in another specific embodiment, $X_2$ is N. In the above embodiment regarding Ar, $X_3$ is CR; in another specific embodiment, $X_3$ is CH; in another specific embodiment, $X_3$ is N. In the above specific embodiment regarding Ar, $X_4$ is CR; in another specific embodiment, $X_4$ is CH; in another specific embodiment, $X_4$ is N.

In the above mentioned embodiment, one of $X_2$, $X_3$ and $X_4$ is C atom that connects the parent core and wherein at least one of them is N; in one specific embodiment, $X_2$ is C atom that connects the parent core, $X_3$ is N; in another specific embodiment, $X_2$ is C atom that connects the parent core, $X_4$ is N; in another specific embodiment, $X_3$ is C atom that connects the parent core, $X_2$ is N; in another specific embodiment, $X_3$ is C atom that connects the parent core, $X_4$ is N; in another specific embodiment, $X_4$ is C atom that connects the parent core, $X_2$ is N; in another specific embodiment, $X_4$ is C atom that connects the parent core, $X_3$ is N.

In another specific embodiment, Ar is

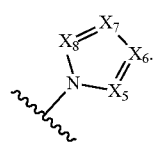

In the above specific embodiment regarding Ar, $X_5$ is CR; in another specific embodiment, $X_5$ is CH; in another specific embodiment, $X_5$ is N. In the above specific embodiment regarding Ar, $X_6$ is CR; in another specific embodiment, $X_6$ is CH; in another specific embodiment, $X_6$ is N. In the above specific embodiment regarding Ar, $X_7$ is CR; in another specific embodiment, $X_7$ is CH; in another specific embodiment, $X_7$ is N. In the above specific embodiment regarding Ar, $X_8$ is CR; in another specific embodiment, $X_8$ is CH; in another specific embodiment, $X_8$ is N.

In more specific embodiment, Ar is the following groups that are optionally substituted by one or two R:

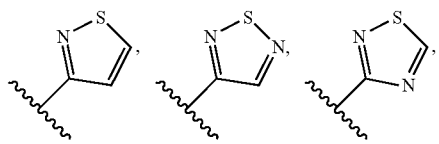

-continued

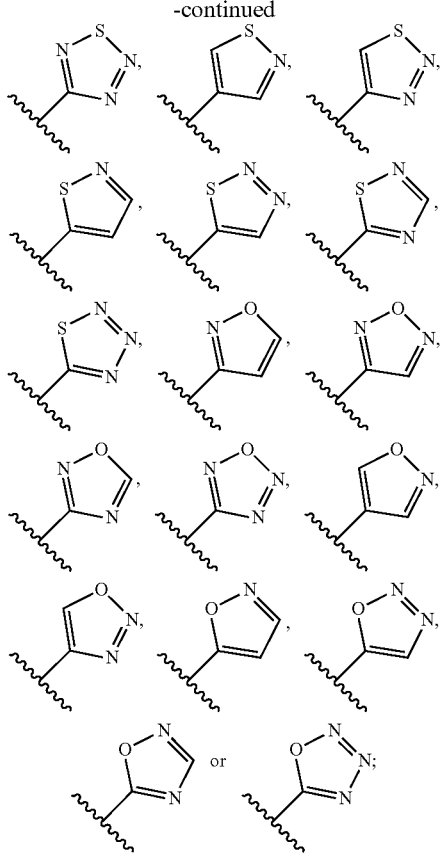

in more specific embodiment, Ar is the following groups that are optionally substituted by one R:

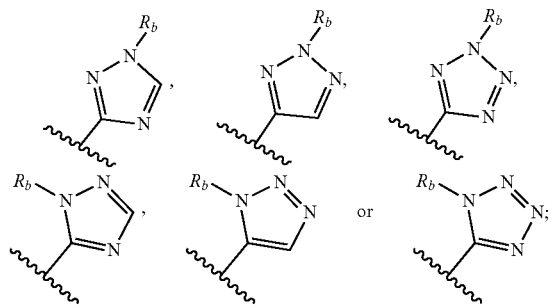

in more specific embodiment, Ar is the following groups that are optionally substituted by R:

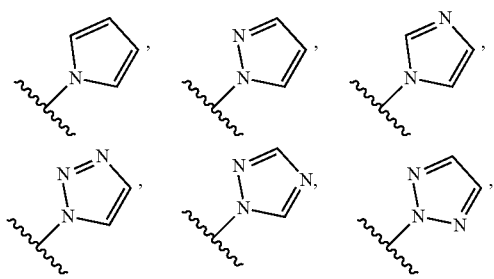

-continued

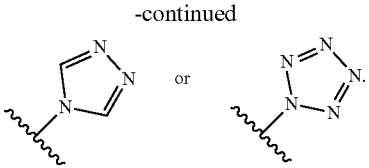

Het, $X_9$, m and n

In one specific embodiment, Het is

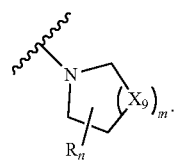

In the above specific embodiment regarding Het, $X_9$ is O; in another specific embodiment, $X_9$ is S; in another specific embodiment, $X_9$ is $NR_b$; in another specific embodiment, $X_9$ is $C(R)_2$. In the above specific embodiment regarding Het, m is 0; in another specific embodiment, m is 1; in another specific embodiment, m is 2. In the above specific embodiment regarding Het, n is 0; in another specific embodiment, n is 1; in another specific embodiment, n is 2; in another specific embodiment, n is 3; in another specific embodiment, n is 4; in another specific embodiment, n is 5; in another specific embodiment, n is 6.

In more specific embodiment, Het is

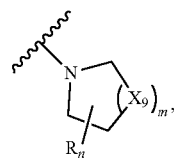

wherein, $X_9$ is $C(R)_2$. In more specific embodiment, Het the following groups that are optionally substituted by one, two, three or more R:

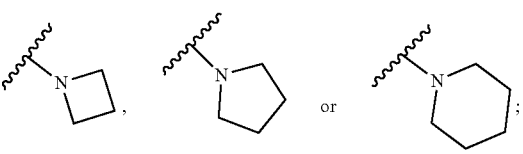 [SMILES: *N1CCC1 ; *N1CCCC1 ; *N1CCCCC1]

in more specific embodiment, Het is selected from the following groups:

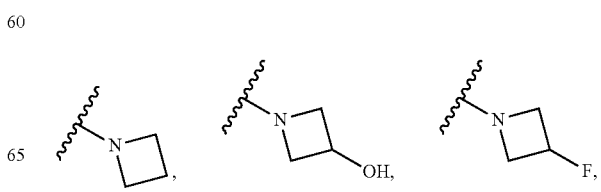

-continued

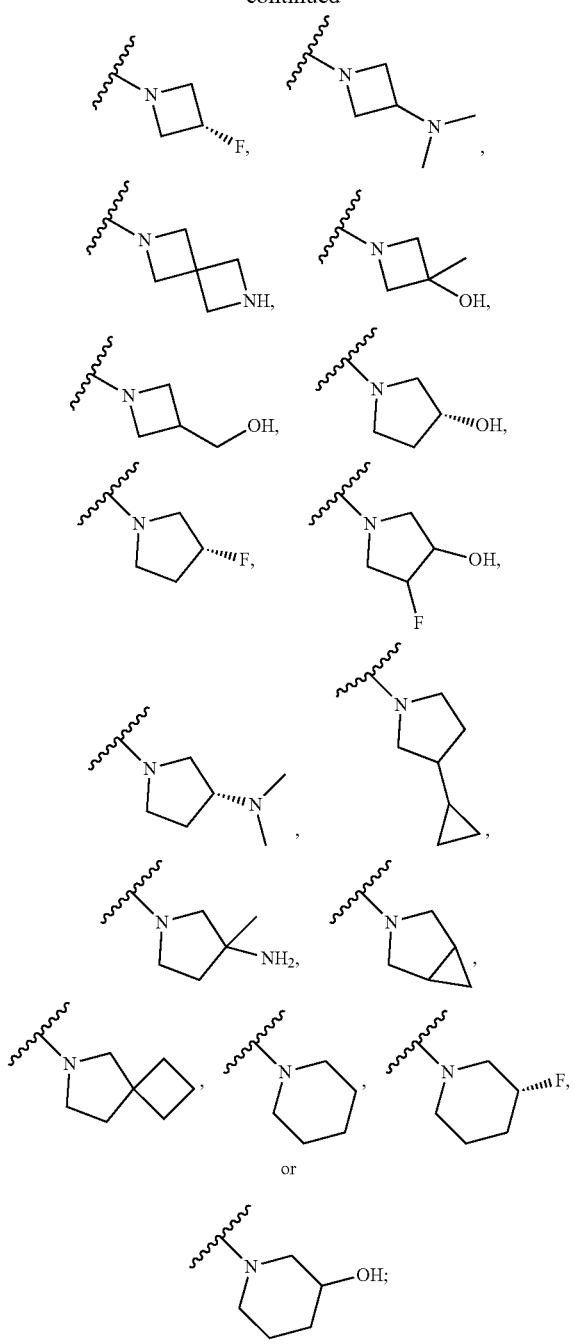

in more specific embodiment, Het is

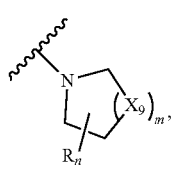

wherein, one $X_9$ is selected from O, S or $NR_b$, and the optionally present other $X_9$ is $C(R)_2$; in more specific embodiment, Het is selected from the following groups:

$R_a$, $R_b$, $R_{1a}$, $R_{2a}$ and R

In one specific embodiment, $R_a$ is independently selected from hydrogen, halo, nitrile, nitro, hydroxy, —NH$_2$, —NHC$_{1-6}$ alkyl, —N(C$_{1-6}$ alkyl)$_2$, C$_{1-6}$ alkyl, C$_{1-6}$ haloalkyl or C$_{1-6}$ alkoxyl; in another specific embodiment, $R_a$ is hydrogen; in another specific embodiment, $R_a$ is halo; in another specific embodiment, $R_a$ is nitrile; in another specific embodiment, $R_a$ is nitro; in another specific embodiment, $R_a$ is hydroxy; in another specific embodiment, $R_a$ is —NH$_2$; in another specific embodiment, $R_a$ is —NHC$_{1-6}$ alkyl; in another specific embodiment, $R_a$ is —N(C$_{1-6}$ alkyl)$_2$; in another specific embodiment, $R_a$ is C$_{1-6}$ alkyl; in another specific embodiment, $R_a$ is C$_{1-6}$ haloalkyl; in another specific embodiment, $R_a$ is C$_{1-6}$ alkoxyl.

In one specific embodiment, $R_b$ is independently selected from hydrogen, C$_{1-6}$ alkyl or C$_{1-6}$ haloalkyl; in another specific embodiment, $R_b$ is hydrogen; in another specific embodiment, $R_b$ is C$_{1-6}$ alkyl; in another specific embodiment, $R_b$ is C$_{1-6}$ haloalkyl.

In one specific embodiment, $R_{1a}$, $R_{2a}$ and R are independently selected from hydrogen, halo, hydroxy, —NH$_2$, —NHC$_{1-6}$ alkyl, —N(C$_{1-6}$ alkyl)$_2$, C$_{1-6}$ alkyl, C$_{1-6}$ haloalkyl, C$_{1-6}$ alkoxyl, C$_{3-7}$ cycloalkyl, C$_{3-7}$ heterocyclyl, C$_{6-10}$ aryl or C$_{5-10}$ heteroaryl; in another specific embodiment, $R_{1a}$, $R_{2a}$ and R are hydrogen; in another specific embodiment, $R_{1a}$, $R_{2a}$ and R are halo; in another specific embodiment, $R_{1a}$, $R_{2a}$ and R are hydroxy; in another specific embodiment, $R_{1a}$, $R_{2a}$ and R are —NH$_2$; in another specific embodiment, $R_{1a}$, $R_{2a}$ and R are —NHC$_{1-6}$ alkyl; in another specific embodiment, $R_{1a}$, $R_{2a}$ and R are —N(C$_{1-6}$ alkyl)$_2$; in another specific embodiment, $R_{1a}$, $R_{2a}$ and R are C$_{1-6}$ alkyl; in another specific embodiment, $R_{1a}$, $R_{2a}$ and R are C$_{1-6}$ haloalkyl; in another specific embodiment, $R_{1a}$, $R_{2a}$ and R are C$_{1-6}$ alkoxyl; in another specific embodiment, $R_{1a}$, $R_{2a}$ and R are C$_{3-7}$ cycloalkyl; in another specific embodiment, $R_{1a}$, $R_{2a}$ and R are C$_{3-7}$ heterocyclyl; in another specific embodiment, $R_{1a}$, $R_{2a}$ and R are C$_{6-10}$ aryl; in another specific embodiment, $R_{1a}$, $R_{2a}$ and R are C$_{5-10}$ heteroaryl.

In one specific embodiment, two R groups on the same or adjacent atoms may together form C$_{3-7}$ cycloalkyl, C$_{3-7}$ heterocyclyl, C$_{6-10}$ aryl or C$_{5-10}$ heteroaryl; in another specific embodiment, two R groups on the same or adjacent atoms may together form C$_{3-7}$ cycloalkyl; in another specific embodiment, two R groups on the same or adjacent atoms may together form C$_{3-7}$ heterocyclyl. In another specific embodiment, two R groups on the same or adjacent atoms may together form C$_{6-10}$ aryl; in another specific embodiment, two R groups on the same or adjacent atoms may together form C$_{5-10}$ heteroaryl.

Any technical solution in any one of the above specific embodiments, or any combination thereof, may be combined with any technical solution in other specific embodiments or any combination thereof. For example, any technical solution of $Y_1$ or any combination thereof may be combined with any technical solution of Y, $R_1$, $R_2$, Z, Ar, $X_1$ to $X_9$, Het, m, n, $R_a$, $R_b$, $R_{1a}$, $R_{2a}$ and R or any combination thereof. The present disclosure is intended to include all combination of such technical solutions, which are not exhaustively listed here to save space.

In specific embodiments, the compounds disclosed herein are selected from the following compounds:

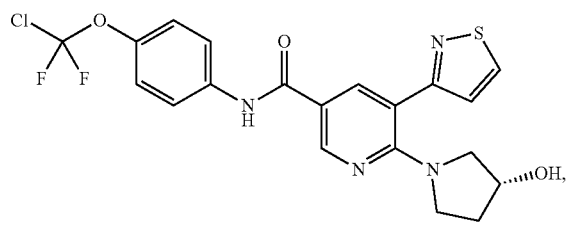

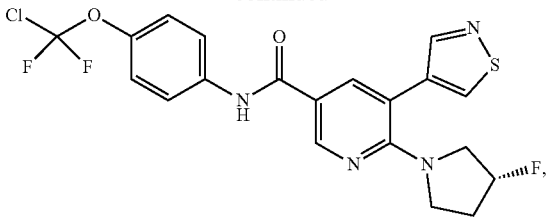

-continued

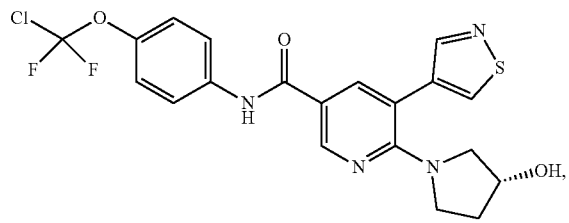

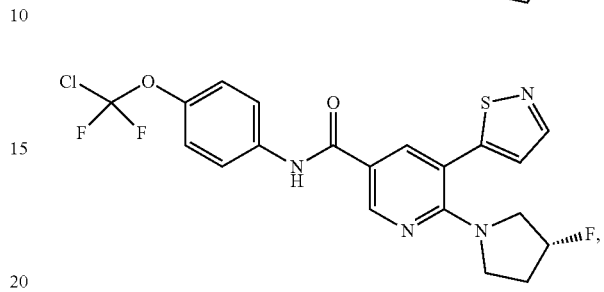

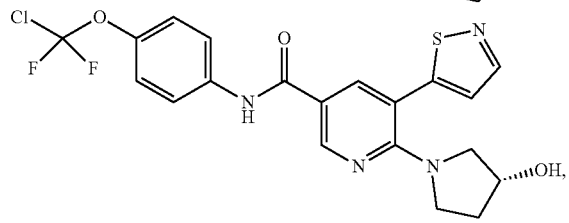

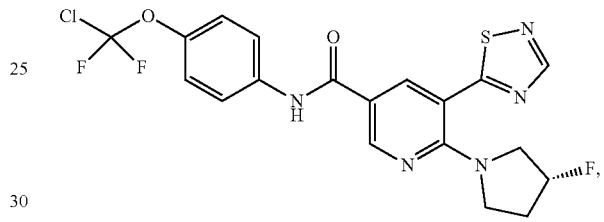

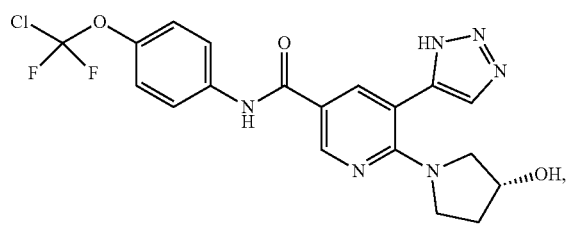

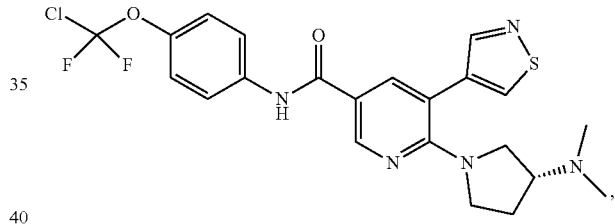

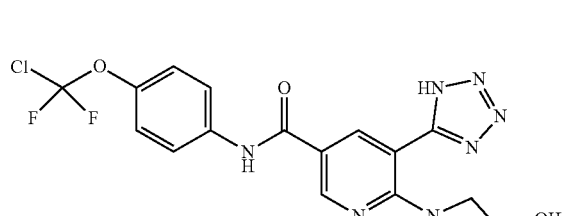

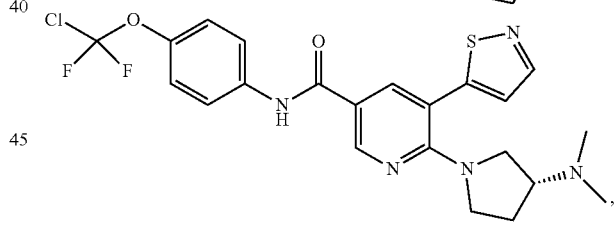

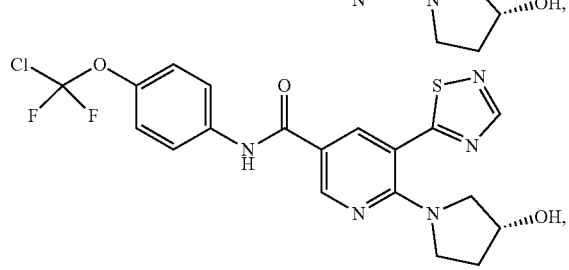

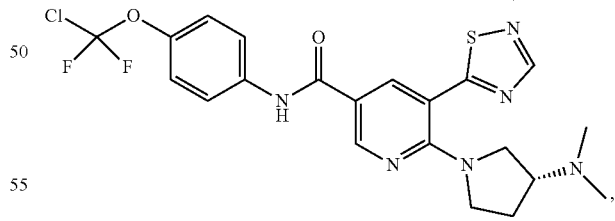

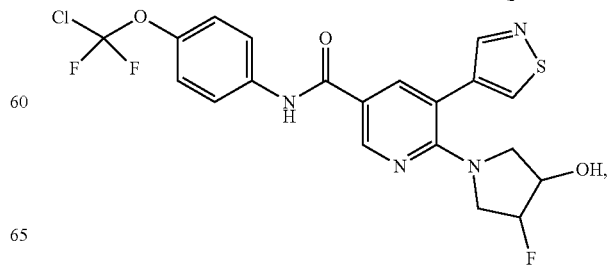

-continued

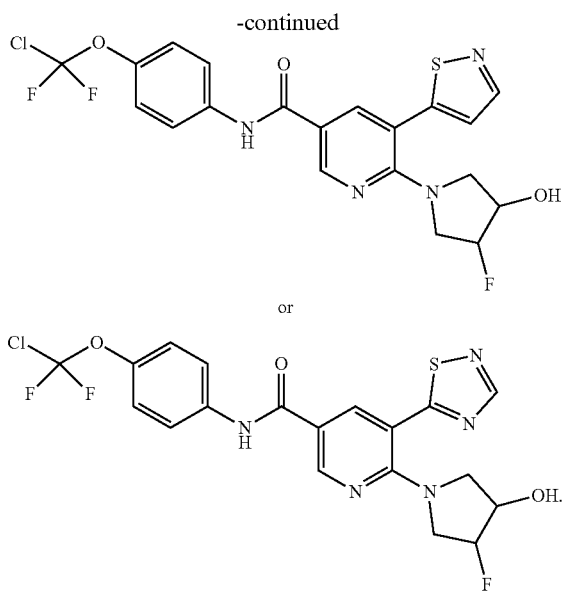

or

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer (such as cis- and trans-isomer), or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses.

Those skilled in the art will appreciate that many organic compounds can form complexes with solvents that react in or precipitate or crystallize from the solvent. These complexes are referred to as "solvates." When the solvent is water, the complex is referred to as a "hydrate." The disclosure encompasses all solvates of the compounds disclosed herein.

Pharmacology and Efficacy

The compounds disclosed herein show therapeutic efficacy especially on diseases or disorders that are dependent on the activity of Bcr-Abl1. In particular, the compounds disclosed herein inhibit the ATP binding site of Bcr-Abl1 (including wild-type Bcr-Abl1 and/or its mutations (including T315I mutations)).

Carcinoma cells utilize invapodia to degrade the extra cellular matrix during tumor invasion and metastasis. Abl kinase activity is required for Src-induced invapodia formation, regulating distinct stages of invapodia assembly and function. The compounds disclosed herein, therefore, as inhibitors of Abl, have the potential to be used as therapies for the treatment of metastatic invasive carcinomas.

An inhibitor of c-Abl kinase can be used to treat brain cancers: including Glioblastoma which is the most common and most aggressive malignant primary brain tumor in which the expression of c-Abl is immunohistochemically detectable in a subset of patients. Therefore a new c-Abl inhibitor with high brain exposure represents a solid therapeutic approach for glioblastoma and other brain cancers.

Compounds disclosed herein can be useful in the treatment of viruses. For example, viral infections can be mediated by Abl1 kinase activity, as in the case of pox viruses and the Ebola virus. Imatinib and nilotinib have been shown to stop the release of Ebola viral particles from infected cells, in vitro. Compounds disclosed herein that inhibit c-Abl kinase, therefore, can be expected to reduce the pathogen's ability to replicate.

Parkinson's disease is the second most prevalent chronic neurodegenerative disease with the most common familial autosomal-recessive form being caused by mutations in the E3 ubiquitin ligase, parkin. Recent studies showed that activated c-ABL was found in the striatum of patients with sporadic Parkinson's disease. Concomitantly, parkin was tyrosine-phosphorylated, causing loss of its ubiquitin ligase and cytoprotective activities as indicated by the accumulation of parkin substrates.

The compounds or compositions disclosed herein are also useful in the treatment of diseases, disorders or conditions mediated by Bcr-Abl kinase: respiratory diseases, allergies, rheumatoid arthritis, osteoarthritis, rheumatic disorders, psoriasis, ulcerative colitis, Crohn's disease, septic shock, proliferative disorders, atherosclerosis, allograft rejection after transplantation, diabetes, stroke, obesity or restenosis, leukemia, stromal tumor, thyroid cancer, systemic mastocytosis, eosinophilia syndrome, fibrosis, polyarthritis, scleroderma, lupus erythematosus, graft versus host disease, neurofibromatosis, pulmonary hypertension, Alzheimer's disease, seminoma, dysgerminoma, mast cell tumor, lung cancer, bronchial carcinoma, dysgerminoma, testicular intraepithelial neoplasia, melanoma, breast cancer, neuroblastoma, papillary/follicular parathyroid hyperplasia/adenoma, colon cancer, colorectal adenoma, ovarian cancer, prostate cancer, glioblastoma, brain tumor, malignant glioma, pancreatic cancer, malignant pleura tumor, hemangioblastoma, hemangioma, kidney cancer, liver cancer, adrenal cancer, bladder cancer, stomach cancer, rectal cancer, vaginal cancer, cervical cancer, endometrial cancer, multiple myeloma, neck and head tumors, neoplasia and other proliferative disease or proliferative diseases, or the combination thereof.

Pharmaceutical Compositions, Formulations and Kits

In another aspect, the disclosure provides a pharmaceutical composition comprising a compound of the present disclosure (also referred to as the "active ingredient") and a pharmaceutically acceptable excipient. In certain embodiments, the pharmaceutical composition comprises an effective amount of the compound of the present disclosure. In certain embodiments, the pharmaceutical composition comprises a therapeutically effective amount of the compound of the present disclosure. In certain embodiments, the pharmaceutical composition comprises a prophylactically effective amount of the compound of the present disclosure.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that can be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (eg, vials, ampoules, bottles, syringes, and/or dispersible packages or other suitable container) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

The following formulation examples illustrate representative pharmaceutical compositions that may be prepared in accordance with this disclosure. The present disclosure, however, is not limited to the following pharmaceutical compositions.

Exemplary Formulation 1—Tablets:

A compound of the present disclosure may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 2—Tablets:

A compound of the present disclosure may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 3—Tablets:

A compound of the present disclosure may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 4—Tablets:

A compound of the present disclosure may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 5—Tablets:

A compound of the present disclosure may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 6—Tablets:

A compound of the present disclosure may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Exemplary Formulation 7—Tablets:

A compound of the present disclosure may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 8—Capsules:

A compound of the present disclosure may be admixed as a dry powder with a starch diluent in an approximate 1:1 weight ratio. The mixture is filled into 250 mg capsules (125 mg of active compound per capsule).

Exemplary Formulation 9—Liquid:

A compound of the present disclosure (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 10—Injection:

A compound of the present disclosure may be dissolved or suspended in a buffered sterile saline injectable aqueous medium to a concentration of approximately 5 mg/mL.

Administration

The pharmaceutical composition provided by the present disclosure can be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present disclosure may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired through the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient (s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds of the present disclosure can also be administered in sustained release forms or from sustained release drug delivery systems. A description of representative sustained release materials can be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are $\alpha$-, $\beta$- and $\gamma$-cyclodextrins consisting of 6, 7 and 8 $\alpha$-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether $\beta$-cyclodextrin, e.g., for example, sulfobutyl ether $\beta$-cyclodextrin, also known as Captisol. See, e.g., U.S. Pat. No. 5,376,645. In certain embodiments, the formulation comprises hexapropyl-$\beta$-cyclodextrin (e.g., 10-50% in water).

Treatment

The compounds disclosed herein are also useful in the treatment of diseases, disorders or conditions mediated by Bcr-Abl kinase: respiratory diseases, allergies, rheumatoid arthritis, osteoarthritis, rheumatic disorders, psoriasis, ulcerative colitis, Crohn's disease, septic shock, proliferative disorders, atherosclerosis, allograft rejection after transplantation, diabetes, stroke, obesity or restenosis, leukemia, stromal tumor, thyroid cancer, systemic mastocytosis, eosinophilia syndrome, fibrosis, polyarthritis, scleroderma, lupus erythematosus, graft versus host disease, neurofibromatosis, pulmonary hypertension, Alzheimer's disease, seminoma, dysgerminoma, mast cell tumor, lung cancer, bronchial carcinoma, dysgerminoma, testicular intraepithelial neoplasia, melanoma, breast cancer, neuroblastoma, papillary/follicular parathyroid hyperplasia/adenoma, colon cancer, colorectal adenoma, ovarian cancer, prostate cancer, glioblastoma, brain tumor, malignant glioma, pancreatic cancer, malignant pleura tumor, hemangioblastoma, hemangioma, kidney cancer, liver cancer, adrenal cancer, bladder cancer, stomach cancer, rectal cancer, vaginal cancer, cervical cancer, endometrial cancer, multiple myeloma, neck and head tumors, neoplasia and other proliferative disease or proliferative diseases, or the combination thereof.

The present disclosure thus provides the use of the compound disclosed herein, especially in the treatment of diseases and disorders mediated by inappropriate Bcr-Abl activity.

The inappropriate Bcr-Abl activity referred to herein is any Bcr-Abl activity that deviates from the normal Bcr-Abl activity expected in a particular mammalian subject. Inappropriate Bcr-Abl activity may take the form of, for instance, an abnormal increase in activity, or an aberration in the timing and or control of Bcr-Abl activity. Such inappropriate activity may result then, for example, from overexpression or mutation of the protein kinase leading to inappropriate or uncontrolled activation.

In a further embodiment, the present disclosure is directed to methods of regulating, modulating, or inhibiting Bcr-Abl for the prevention and/or treatment of disorders related to unregulated or inappropriate Bcr-Abl activity.

In another embodiment, the said disorder mediated by Bcr-Abl activity is respiratory diseases. In another embodiment, the said disorder is proliferative diseases. In yet another embodiment, the said disorder is cancer. In another embodiment, the said disorder is leukemia.

In another embodiment, compounds disclosed herein can also be useful in the treatment of neural degeneration. While native c-ABL tyrosine kinase remains relatively quiescent in healthy adult brain, it can be activated in the brain of patients with CNS diseases, including neurodegenerative diseases such as, Alzheimer's disease (AD), Parkinson's disease (AD), frontotemporal dementia (FTD), Picks disease, Niemann-Pick type C disease (NPC) and other degenerative, inflammatory and autoimmune diseases and ageing.

An effective amount of a compound disclosed herein will generally be administered in a single or multiple doses at an average daily dose of from 0.01 mg to 50 mg of compound per kilogram of patient body weight, preferably from 0.1 mg to 25 mg of compound per kilogram of patient body weight. In general, the compounds disclosed herein may be administered to a patient in need of such treatment in a daily dosage range of from about 1 mg to about 3500 mg per patient, preferably from 10 mg to 1000 mg. For example, the daily dose per patient can be 10, 20, 30, 40, 50, 60, 70, 80, 90, 100, 150, 200, 250, 300, 350, 400, 500, 600, 700, 800, 900 or 1000 mg. It can be administered one or more times daily, weekly (or several days apart) or on an intermittent schedule. For example, the compound can be administered one or more times per day on a weekly basis (e.g., every Monday), continually or for several weeks, such as 4-10 weeks. Alternatively, the administration may be continued for several days (e.g., 2-10 days), followed by a few days (e.g., 1-30 days) without administration of the compound, and the cycle may be repeated indefinitely or repeated for a given number of times, such as 4-10. Cycles. For example, the compounds disclosed herein may be administered daily for 5 days, then intermittently for 9 days, then administered daily for 5 days, then intermittent for 9 days, and so on, and the cycle is repeated indefinitely or repeated 4-10 times.

EXAMPLES

The following examples are provided to provide those skilled in the art with a complete disclosure and description of how to carry out, prepare and evaluate the methods and compounds claimed herein, which are only for illustrative purpose and not constitute any limitation of the scope of the invention.

Synthetic Method

The compounds of the present disclosure can be prepared according to conventional methods in the art and using suitable reagents, starting materials, and purification methods known to those skilled in the art.

The preparation of the compounds of formula (I) of the present disclosure is more specifically described below, but these specific methods do not constitute any limitation to the present disclosure. The compounds of the present disclosure may also be conveniently prepared by combining various synthetic methods described in the specification or known in the art, and such combinations are readily available to those skilled in the art to which the present disclosure pertains.

Usually, in the preparation, each reaction is usually carried out in an inert solvent at room temperature to reflux temperature (e.g., 0° C. to 100° C., preferably 0° C. to 80° C.). The reaction time is usually from 0.1 to 60 hours, preferably from 0.5 to 24 hours.

Example 1 Preparation of (R)-6-(3-hydroxypyrrolidin-1-yl)-5-(isothiazol-3-yl)-N-(4-(chlorodifluoromethoxy)phenyl) nicotinamide (Compound 6)

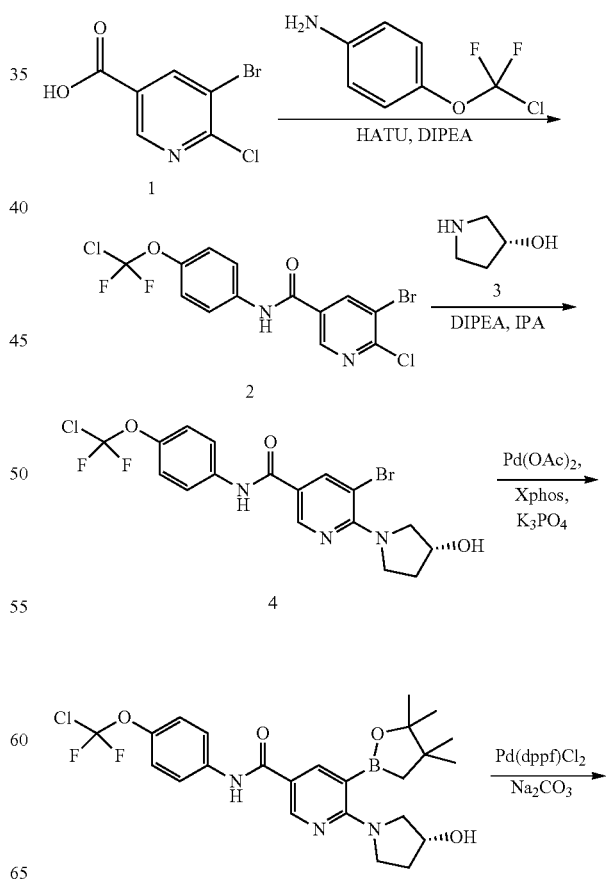

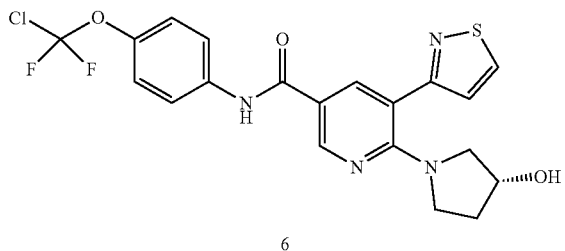

6

Step 1: Synthesis of 6-chloro-5-bromo-N-(4-(chlorodifluoromethoxy)phenyl)nicotinamide (Compound 2)

To a reaction flask were added 6-chloro-5-bromonicotinic acid (1.17 g, 4.97 mmol), 4-(chlorodifluoromethoxy)aniline (0.8 g, 4.15 mmol), dissolved with 20 mL anhydrous DMF, 2-(7-aza-1H-benzotriazol-1-yl)-1,1,3,3-tetramethyluronium hexafluorophosphate (HATU, 2.1 g, 5.39 mmol) and N,N-diisopropylethylamine (DIPEA, 534 mg, 4.15 mmol) were added, and the reaction was stirred under nitrogen protection at room temperature for 18 hours. The reaction was diluted with large amount of water, extracted with ethyl acetate for 3-4 times, the organic layers were combined, washed with brine, concentrated, purified by column chromatography, dried in vacuum to afford 1.18 g of a product, yield: 69.5%.

Step 2: Synthesis of (R)-6-(3-hydroxypyrrolidin-1-yl)-5-bromo-N-(4-(chlorodifluoromethoxy)phenyl) nicotinamide (Compound 4)

To a reaction flask were added compound 2 (0.92 g, 2.0 mmol) and (R)-3-hydroxypyrrolidine (209.1 mg, 2.4 mmol), 2 ml isopropyl alcohol was added, DIPEA (568.7 mg, 4.4 mmol) was added, and the reaction was heated to 140° C. and stirred for 2 hours. The temperature was cooled to room temperature, concentrated to remove solvent, purified by silica gel column chromatography to afford 813 mg of a product, yield: 88.2%.

Step 3: Synthesis of (R)-6-(3-hydroxypyrrolidin-1-yl)-5-(4,4,5,5-tetramethyl-1,3,2-dioxaborolan-2-yl)-N-(4-(chloro difluoromethoxy)phenyl)nicotinamide (Compound 5)

In a reaction flask were added compound 4 (322.7 mg, 0.7 mmol), bis(pinacolato)diboron (711.03 mg, 2.8 mmol), palladium acetate (4.71 mg, 0.021 mmol), Xphos (25.0 mg, 0.053 mmol) and potassium phosphate (445.8 mg, 2.1 mmol), dissolved in 10 mL anhydrous dioxane, and the reaction was heated to 60° C. in microwave and reacted for 4 hours. TLC detected the starting material was not completely consumed, bis(pinacolato)diboron (356 mg, 1.4 mmol) was additionally added and reacted at 60° C. overnight. TLC detected the reaction was complete, the reaction was concentrated, purified by silica gel column chromatography to afford 262 mg of a product, yield: 73.5%.

Step 4: Synthesis of (R)-6-(3-hydroxypyrrolidin-1-yl)-5-(isothiazol-3-yl)-N-(4-(chlorodifluoromethoxy)phenyl)nicotinamide (Compound 6)

To a reaction flask were added compound 5 (200 mg, 0.392 mmol), 3-bromoisothiazole (96 mg, 0.588 mmol), Pd(dppf)Cl$_2$ (32 mg, 0.02 mmol) and sodium carbonate (126 mg, 1.18 mmol), 2 mL glycol dimethyl ether and 0.4 mL water were added, bubbled with nitrogen gas for 10 minutes, heated to 120° C. in microwave and reacted for 0.5 hour. After TLC detected the reaction was complete, the reaction was concentrated, purified by silica gel column chromatography to afford 84 mg of a product, yield: 46%. LC-MS (APCI): m/z=467.3(M+1)$^+$; $^1$H NMR (400 MHz, DMSO) δ 10.17 (s, 1H), 9.04 (s, 1H), 8.90 (s, 1H), 8.76 (d, J=2.3 Hz, 1H), 8.05 (d, J=2.3 Hz, 1H), 7.86 (d, J=9.1 Hz, 2H), 7.33 (d, J=8.8 Hz, 2H), 4.86 (d, J=3.4 Hz, 1H), 4.21 (s, 1H), 3.41 (dd, J=17.0, 9.3 Hz, 1H), 3.29-3.18 (m, 2H), 2.90 (d, J=11.1 Hz, 1H), 1.89-1.80 (m, 1H), 1.75 (s, 1H).

Example 2 Preparation of (R)-6-(3-hydroxypyrrolidin-1-yl)-5-(isothiazol-4-yl)-N-(4-(chlorodifluoromethoxy)phenyl) nicotinamide (Compound 7)

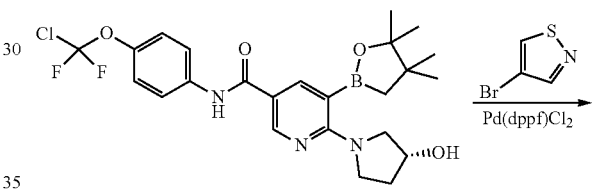

5

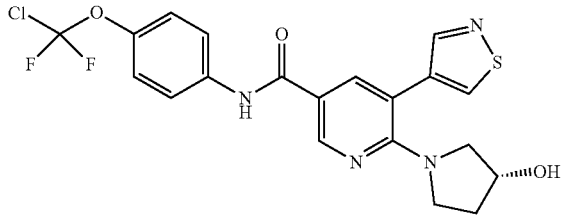 [SMILES: O=C(Nc1ccc(OC(F)(F)Cl)cc1)c1cnc(N2CC[C@@H](O)C2)c(-c2cnsc2)c1]

7

To a reaction flask were added compound 5 (200 mg, 0.392 mmol), 4-bromoisothiazole (96 mg, 0.588 mmol), Pd(dppf)Cl$_2$ (32 mg, 0.02 mmol) and sodium carbonate (126 mg, 1.18 mmol), 2 mL glycol dimethyl ether and 0.4 mL water were added, bubbled with nitrogen gas for 10 minutes, and the reaction was heated to 120° C. in microwave for half an hour. After TLC detected the reaction was complete, the reaction was concentrated, purified by silica gel column chromatography to afford 58 mg of a product, yield: 31.7%. LC-MS(APCI): m/z=467.3(M+1)$^+$; $^1$H NMR (400 MHz, DMSO) δ 10.17 (s, 1H), 9.04 (s, 1H), 8.76 (d, J=2.3 Hz, 1H), 8.70 (s, 1H), 8.05 (d, J=2.3 Hz, 1H), 7.86 (d, J=9.1 Hz, 2H), 7.33 (d, J=8.8 Hz, 2H), 4.86 (d, J=3.4 Hz, 1H), 4.21 (s, 1H), 3.41 (dd, J=17.0, 9.3 Hz, 1H), 3.29-3.18 (m, 2H), 2.90 (d, J=11.1 Hz, 1H), 1.89-1.80 (m, 1H), 1.75 (s, 1H).

Example 3 Preparation of (R)-6-(3-hydroxypyrrolidin-1-yl)-5-(isothiazol-5-yl)-N-(4-(chlorodifluoromethoxy)phenyl) nicotinamide (Compound 8)

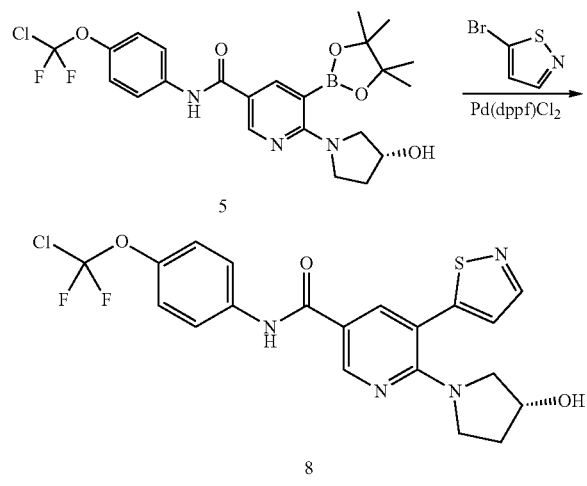

To a reaction flask were added compound 5 (200 mg, 0.392 mmol), 5-bromoisothiazole (96 mg, 0.588 mmol), Pd(dppf)Cl$_2$ (32 mg, 0.02 mmol) and sodium carbonate (126 mg, 1.18 mmol), 2 mL glycol dimethyl ether and 0.4 mL water were added, bubbled with nitrogen gas for 10 minutes, and the reaction was heated to 120° C. in microwave for half an hour. After TLC detected the reaction was complete, the reaction was concentrated, purified by silica gel column chromatography to afford 97 mg of a product, yield: 53.1%. LC-MS(APCI): m/z=467.3(M+1)$^+$; $^1$H NMR (400 MHz, DMSO) δ 10.17 (s, 1H), 9.04 (s, 1H), 8.90 (s, 1H), 8.76 (d, J=2.3 Hz, 1H), 8.35 (d, J=2.3 Hz, 1H), 7.86 (d, J=9.1 Hz, 2H), 7.33 (d, J=8.8 Hz, 2H), 4.86 (d, J=3.4 Hz, 1H), 4.21 (s, 1H), 3.41 (dd, J=17.0, 9.3 Hz, 1H), 3.29-3.18 (m, 2H), 2.90 (d, J=11.1 Hz, 1H), 1.89-1.80 (m, 1H), 1.75 (s, 1H).

Example 4 Preparation of (R)-6-(3-hydroxypyrrolidin-1-yl)-5-(1H-1,2,3-triazol-5-yl)-N-(4-(chlorodifluoromethoxy)phenyl)nicotinamide (Compound 12)

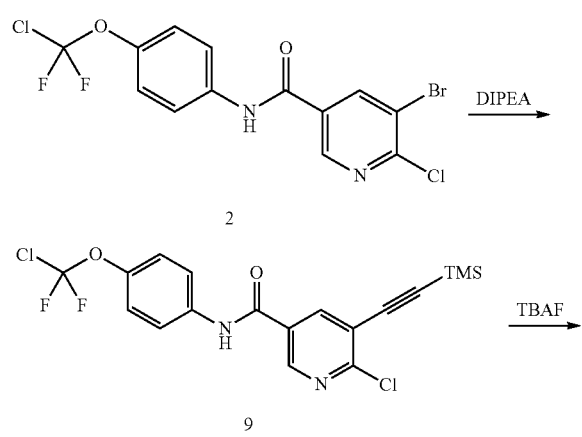

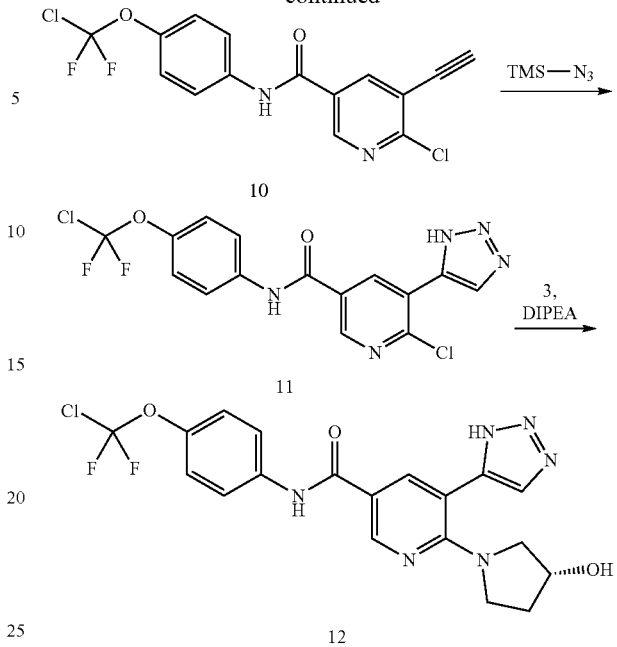

Step 1: Synthesis of 6-chloro-5-(2-trimethylsilylethyn-1-yl)-N-(4-(chlorodifluoromethoxy)phenyl) nicotinamide (Compound 9)

To a reaction flask were added compound 2 (400 mg, 0.97 mmol), trimethylsilylethyne (143.4 mg, 1.46 mmol), Pd(PPh$_3$)$_2$Cl$_2$ (34 mg, 0.048 mmol), Copper iodide (18.4 mg, 0.096 mmol) and DIPEA (377 mg, 2.92 mmol), 10 mL anhydrous tetrahydrofuran was added to dissolve the substances, and the reaction was heated under nitrogen protection in microwave to 120° C. for 1 hour. After TLC detected the reaction was complete, the reaction was concentrated, purified by silica gel column chromatography to afford 250 mg of a product, yield: 60.2%.

Step 2: Synthesis of 6-chloro-5-ethynyl-N-(4-(chlorodifluoromethoxy)phenyl)nicotinamide (Compound 10)

To a reaction flask were added compound 9 (250 mg, 0.58 mmol), 10 mL anhydrous tetrahydrofuran was added to dissolve the substances, 1M tetrabutylammonium fluoride in tetrahydrofuran (1.17 mL, 1.17 mmol) was added, and the reaction was reacted under nitrogen protection at room temperature for 20 minutes. After TLC detected the reaction was complete, the reaction was concentrated, purified by silica gel column chromatography to afford 194.5 mg of a product, yield: 94.2%.

Step 3: Synthesis of 6-chloro-5-(1H-1,2,3-triazol-5-yl)-N-(4-(chlorodifluoromethoxy)phenyl)nicotinamide (Compound 11)

To a reaction flask were added compound 10 (127 mg, 0.357 mmol) and azidotrimethylsilane (82.2 mg, 0.713 mmol), 2 mL anhydrous toluene was added to dissolve the substances, and the reaction was heated under nitrogen protection to 120° C. for 48 hours. The reaction was concentrated, purified by silica gel column chromatography to afford 45 mg of a product, yield: 31.6%.

Step 4: Synthesis of (R)-6-(3-hydroxypyrrolidin-1-yl)-5-(1H-1,2,3-triazol-5-yl)-N-(4-(chlorodifluoromethoxy)phenyl)nicotinamide (Compound 12)

To a reaction flask were added compound 11 (30 mg, 0.075 mmol) and (R)-3-hydroxypyrrolidine (7.86 mg, 0.09 mmol), 2 mL isopropyl alcohol was added, followed by DIPEA (21.32 mg, 0.165 mmol), and the reaction was heated to 140° C. and stirred for 2 hours. The reaction was cooled to room temperature, concentrated to remove solvent, purified by silica gel column chromatography to afford 27.3 mg of a product, yield: 81%. LC-MS(APCI): m/z=451.5 (M+1)+; 1H NMR (400 MHz, DMSO) δ 10.22 (s, 1H), 8.75 (d, J=2.4 Hz, 1H), 8.25 (s, 1H), 8.07 (d, J=2.3 Hz, 1H), 7.89 (d, J=9.1 Hz, 2H), 7.31 (d, J=8.9 Hz, 2H), 4.81 (s, 1H), 4.14 (s, 1H), 3.50-3.42 (m, 1H), 3.23-3.14 (m, 2H), 2.80 (d, J=11.8 Hz, 1H), 1.79 (dd, J=8.9, 4.4 Hz, 1H), 1.73-1.63 (m, 1H).

Example 5 Preparation of (R)-6-(3-hydroxypyrrolidin-1-yl)-5-(1H-1,2,3,4-tetrazol-5-yl)-N-(4-(chlorodifluoromethoxy)phenyl)nicotinamide (Compound 16)

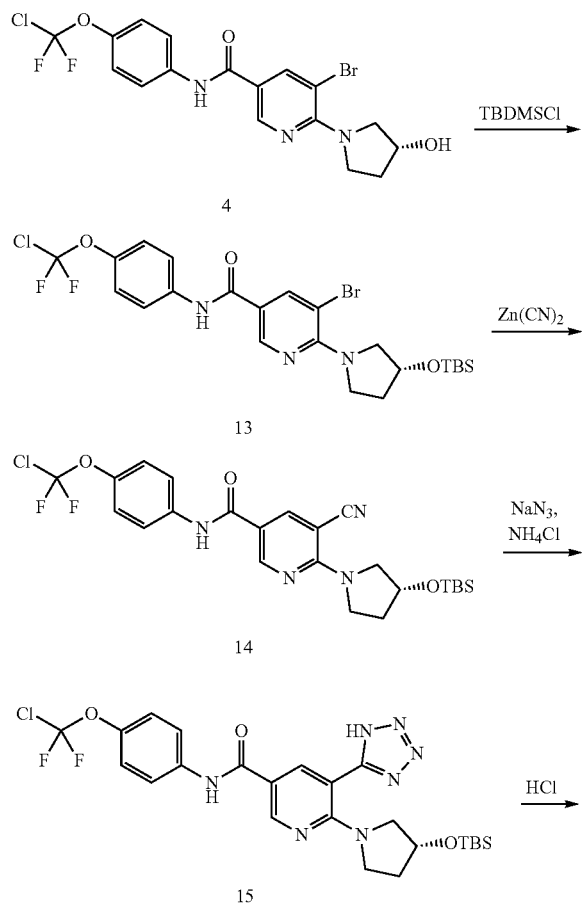

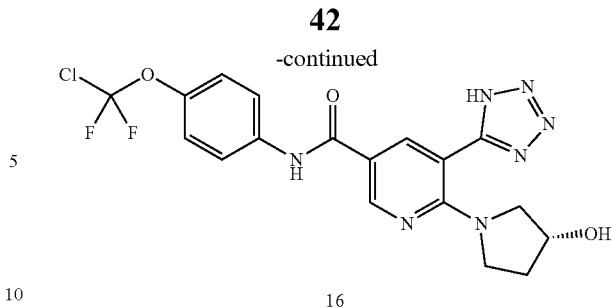

Step 1: Synthesis of (R)-6-(3-tert-butyldimethylsilyloxypyrrolidin-1-yl)-5-bromo-N-(4-(chlorodifluoromethoxy)phenyl)nicotinamide (Compound 13)

To a reaction flask were added compound 4 (200 mg, 0.434 mmol), tert-butyldimethylsilyl chloride (100 mg, 0.65 mmol) and imidazole (100 mg, 1.47 mmol), 5 mL anhydrous DMF was added, and the reaction was stirred at room temperature for 1 hour. After TLC detected the reaction was complete, water was added to dilute the reaction, which was extracted with ethyl acetate for 3-4 times, the organic layers were combined, washed with brine, concentrated and purified by silica gel column chromatography to afford 248 mg of a product, yield: 99%.

Step 2: Synthesis of (R)-6-(3-tert-butyldimethylsilyloxypyrrolidin-1-yl)-5-cyano-N-(4-(chlorodifluoromethoxy)phenyl)nicotinamide (Compound 14)

To a reaction flask were added compound 13 (317 mg, 0.551 mmol), zinc cyanide (65 mg, 0.551 mmol) and tetrakis(triphenylphosphine)palladium (19 mg, 0.0165 mmol), 5 mL anhydrous DMF was added, and the reaction was heated to 150° C. in microwave and reacted for 10 minutes. After TLC detected the reaction was complete, water was added to dissolve the substances, which was extracted with ethyl acetate for 3-4 times, the organic layers were combined, washed with brine, concentrated and purified by silica gel column chromatography to afford 209 mg of a product, yield: 93%.

Step 3: Synthesis of (R)-6-(3-tert-butyldimethylsilyloxypyrrolidin-1-yl)-5-(1H-1,2,3,4-tetrazol-5-yl)-N-(4-(chlorodi fluoromethoxy)phenyl)nicotinamide (Compound 15)

To a reaction flask were added compound 14 (209 mg, 0.4 mmol), sodium azide (312 mg, 4.8 mmol) and ammonium chloride (254 mg, 4.8 mmol), 5 mL anhydrous DMF was added, and the reaction was heated to 150° C. and reacted overnight. Water was added to dilute the reaction, which was extracted with ethyl acetate for 3-4 times, the organic layers were combined, washed with brine, concentrated and purified by silica gel column chromatography to afford 102 mg of a product, yield: 45.1%.

Step 4: Synthesis of (R)-6-(3-hydroxypyrrolidin-1-yl)-5-(1H-1,2,3,4-tetrazol-5-yl)-N-(4-(chloro difluoromethoxy)phenyl)nicotinamide (Compound 16)

To a reaction flask were added compound 15 (102 mg, 0.18 mmol), 3 mL methanol was added to dissolve it, 4N HCl in methanol (0.225 ml, 0.9 mmol) was added, and the reaction was stirred at room temperature for 0.5 hour. The reaction was concentrated and purified by silica gel column chromatography to afford 67.4 mg of a product, yield: 83%. LC-MS(APCI): m/z=452.4(M+1)+; 1H NMR (400 MHz, DMSO) δ 10.22 (s, 1H), 8.75 (d, J=2.4 Hz, 1H), 8.07 (d, J=2.3 Hz, 1H), 7.89 (d, J=9.1 Hz, 2H), 7.31 (d, J=8.9 Hz, 2H), 4.81 (s, 1H), 4.14 (s, 1H), 3.50-3.42 (m, 1H), 3.23-3.14 (m, 2H), 2.80 (d, J=11.8 Hz, 1H), 1.79 (dd, J=8.9, 4.4 Hz, 1H), 1.73-1.63 (m, 1H).

Example 6 Preparation of (R)-6-(3-hydroxypyrrolidin-1-yl)-5-(1,2,4-thiodiazol-5-yl)-N-(4-(chlorodifluoromethoxy)phenyl)nicotinamide (Compound 20)

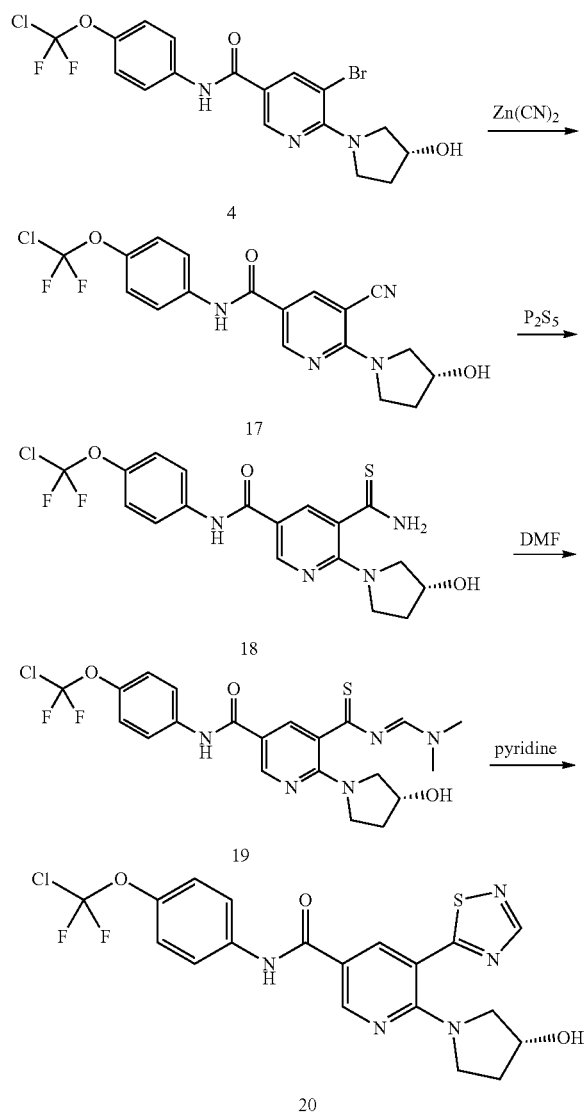

Step 1: Synthesis of (R)-6-(3-hydroxypyrrolidin-1-yl)-5-cyano-N-(4-(chloro difluoromethoxy)phenyl)nicotinamide (Compound 17)

To a reaction flask were added compound 4 (92.2 mg, 0.2 mmol), zinc cyanide (23.5 mg, 0.2 mmol) and tetrakis(triphenylphosphine)palladium (7 mg, 0.006 mmol), 2 mL anhydrous DMF was added, and the reaction was heated to 150° C. in microwave and reacted for 10 minutes. After TLC detected the reaction was complete, water was added to dilute the reaction, which was extracted with ethyl acetate for 3-4 times, the organic layers were combined, washed with brine, concentrated and purified by silica gel column chromatography to afford 77.5 mg of a product, yield: 95%.

Step 2: Synthesis of (R)-6-(3-hydroxypyrrolidin-1-yl)-5-aminothioformyl-N-(4-(chlorodifluoromethoxy)phenyl)nicotinamide (Compound 18)

To a reaction flask were added compound 17 (250 mg, 0.612 mmol) and phosphorus pentasulfide (117 mg, 1.838 mmol), 10 mL ethanol was added, and the reaction was heated to 90° C. and reacted for 18 hours. The reaction was concentrated to remove solvent, purified by silica gel column chromatography to afford 75 mg of a product, yield: 27.7%.

Step 3: Synthesis of (R)-6-(3-hydroxypyrrolidin-1-yl)-5-((dimethylamino)methyleneaminothioformyl)-N-(4-(chlorodifluoromethoxy)phenyl)nicotinamide (Compound 19)

To a reaction flask were added compound 18 (75 mg, 0.178 mmol) and N,N-dimethylformamide dimethyl acetal (64 mg, 0.534 mmol), 5 mL anhydrous DMF was added, and the reaction was stirred at room temperature for 10 minutes. After TLC detected the reaction was complete, water was added to dilute the reaction, extracted with ethyl acetate for 3-4 times, the organic layers were combined, washed with brine, concentrated and purified by silica gel column chromatography to afford 40 mg of a product, yield: 45.2%.

Step 4: Synthesis of (R)-6-(3-hydroxypyrrolidin-1-yl)-5-(1,2,4-thiodiazol-5-yl)-N-(4-(chlorodifluoromethoxy)phen yl)nicotinamide (Compound 20)

To a reaction flask were added compound 19 (40 mg, 0.08 mmol) and pyridine (12.6 mg, 0.16 mmol), 2.5 mL ethanol was added to dissolve it, hydroxylamine-O-sulfonic acid (10 mg, 0.088 mmol) in 1.5 mL methanol was slowly added dropwise, and after addition the reaction was stirred at room temperature for 1 hour. After TLC detected the reaction was complete, concentrated to remove solvent, purified by silica gel column chromatography to afford 21 mg of a product, yield: 56.1%. LC-MS(APCI): m/z=468.6(M+1)+; 1H NMR (400 MHz, DMSO) δ 10.31 (s, 1H), 9.01 (s, 1H), 8.88 (d, J=2.3 Hz, 1H), 8.33 (d, J=2.3 Hz, 1H), 7.87 (d, J=9.1 Hz, 2H), 7.35 (d, J=8.9 Hz, 2H), 5.32 (t, J=4.8 Hz, 1H), 4.27 (s, 1H), 3.56 (d, J=7.4 Hz, 1H), 3.28 (dd, J=13.2, 5.3 Hz, 2H), 2.93 (d, J=12.0 Hz, 1H), 1.92-1.85 (m, 1H), 1.80 (dt, J=15.9, 6.5 Hz, 1H.

Example 7 Preparation of (R)-6-(3-fluoropyrrolidin-1-yl)-5-(isothiazol-4-yl)-N-(4-(chlorodifluoromethoxy)phenyl)nicotinamide (Compound 23)

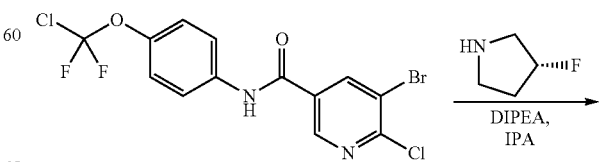

-continued

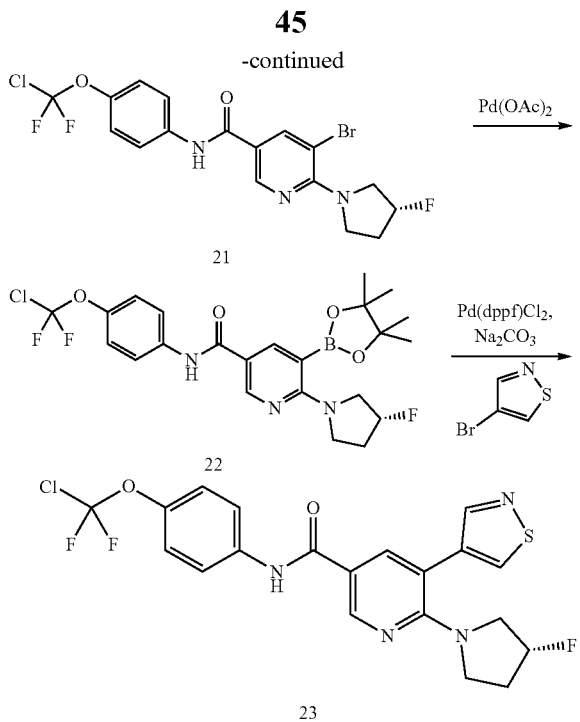

Step 1: Synthesis of (R)-6-(3-fluoropyrrolidin-1-yl)-5-bromo-N-(4-(chlorodifluoromethoxy)phenyl)nicotinamide (Compound 21)

To a reaction flask were added compound 2 (0.90 g, 2.19 mmol) and (R)-3-fluoropyrrolidine hydrochloride (330 mg, 2.63 mmol), 15 mL isopropyl alcohol, and DIPEA (621 mg, 4.82 mmol) were added, and the reaction was heated to 140° C. and stirred for 2 hours. After cooling to room temperature, the reaction was concentrated to remove solvent, purified by silica gel column chromatography to afford 841 mg of a product, yield: 83%.

Step 2: Synthesis of (R)-6-(3-fluoropyrrolidin-1-yl)-5-(4,4,5,5-tetramethyl-1,3,2-dioxaborolan-2-yl)-N-(4-(chlorodi fluoromethoxy)phenyl)nicotinamide (Compound 22)

In a reaction flask were added compound 21 (628 mg, 1.35 mmol), bis(pinacolato)diboron (1.03 g, 4.06 mmol), palladium acetate (10 mg, 0.041 mmol), Xphos (50 mg, 0.101 mmol) and potassium phosphate (861 mg, 4.06 mmol), 20 mL anhydrous dioxane was added to dissolve the substances, and the reaction was heated to 60° C. in microwave and reacted for 4 hours. TLC detected the starting material was not completely consumed, bis(pinacolato)diboron (1.03 g, 4.06 mmol) was additionally added and then reacted at 60° C. overnight. After TLC detected the reaction was complete, the reaction was concentrated, purified by silica gel column chromatography to afford 514.3 mg of a product, yield: 75%.

Step 3: Synthesis of (R)-6-(3-fluoropyrrolidin-1-yl)-5-(isothiazol-4-yl)-N-(4-(chlorodifluoromethoxy)phenyl)nicotinamide (Compound 23)

To a reaction flask were added compound 22 (100 mg, 0.195 mmol), 4-bromoisothiazole (50 mg, 0.293 mmol), Pd(dppf)Cl$_2$ (5 mg, 0.006 mmol) and sodium carbonate (60 mg, 0.558 mmol), 5 mL glycol dimethyl ether and 0.9 mL water were added, bubbled with nitrogen gas for 10 minutes, and the reaction was heated to 100° C. in microwave and reacted for half an hour. After TLC detected the reaction was complete, the reaction was concentrated, purified by silica gel column chromatography to afford 42 mg of a product, yield: 46%. LC-MS(APCI): m/z=469.5 (M+1)$^+$. $^1$H NMR (400 MHz, CDCl$_3$) δ 8.69 (d, J=2.4 Hz, 1H), 8.58 (d, J=9.6 Hz, 2H), 7.94 (d, J=2.4 Hz, 1H), 7.74 (s, 1H), 7.67 (d, J=9.0 Hz, 2H), 7.23 (s, 1H), 5.21 (d, J=52.0 Hz, 1H), 3.56 (d, J=3.1 Hz, 1H), 3.52-3.44 (m, 2H), 3.30 (t, J=9.7 Hz, 1H), 2.26-2.19 (m, 1H), 2.03-1.97 (m, 1H).

Example 8 Preparation of (R)-6-(3-fluoropyrrolidin-1-yl)-5-(isothiazol-5-yl)-N-(4-(chlorodifluoromethoxy)phenyl)nicotinamide (Compound 24)

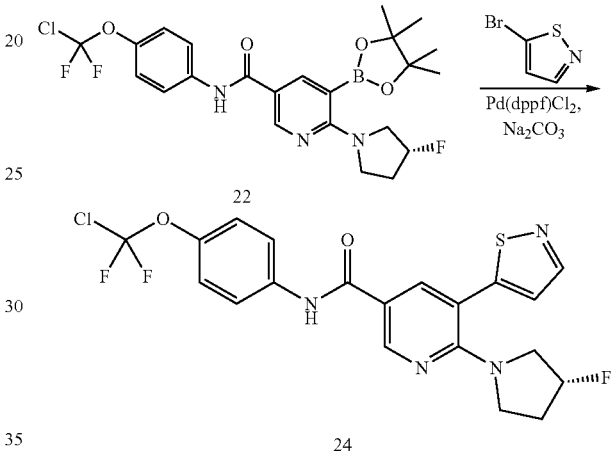

To a reaction flask were added compound 22 (100 mg, 0.195 mmol), 5-bromoisothiazole (50 mg, 0.293 mmol), Pd(dppf)Cl$_2$ (5 mg, 0.006 mmol) and sodium carbonate (60 mg, 0.558 mmol), 5 mL glycol dimethyl ether and 0.9 mL water were added, bubbled with nitrogen gas for 10 minutes, and the reaction was heated to 100° C. in microwave and reacted for half an hours. After TLC detected the reaction was complete, the reaction was concentrated, purified by silica gel column chromatography to afford 45 mg of a product, yield: 48%. LC-MS(APCI): m/z=469.5 (M+1)$^+$. $^1$H NMR (400 MHz, CDCl$_3$) δ 8.73 (d, J=2.3 Hz, 1H), 8.49 (d, J=1.4 Hz, 1H), 7.97 (d, J=2.3 Hz, 1H), 7.90 (s, 1H), 7.66 (d, J=9.0 Hz, 2H), 7.24 (s, 1H), 7.23-7.20 (m, 2H), 5.30 (s, 1H), 3.66 (dd, J=13.6, 3.2 Hz, 1H), 3.60-3.53 (m, 2H), 3.36 (t, J=9.8 Hz, 1H), 2.29-2.18 (m, 1H), 2.10-1.94 (m, 1H).

Example 9 Preparation of (R)-6-(3-fluoropyrrolidin-1-yl)-5-(1,2,4-thiodiazol-5-yl)-N-(4-(chlorodifluoromethoxy)phenyl)nicotinamide (Compound 28)

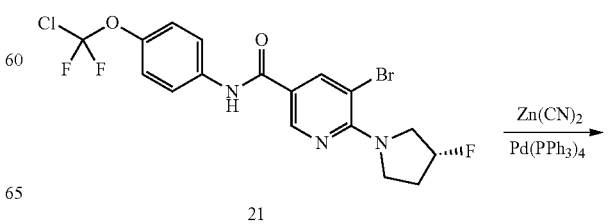

-continued

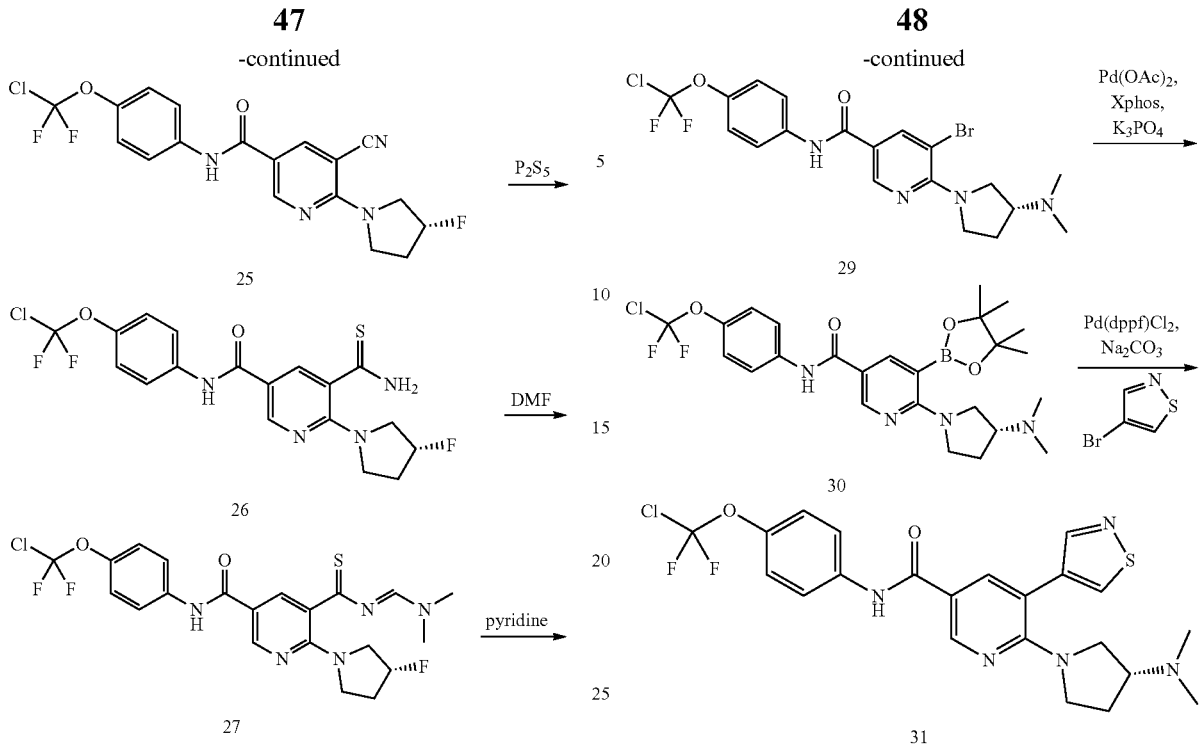

According to the same procedures as those used in the preceding Examples, the title product compound 28 was obtained. LC-MS(APCI): m/z=470.8 (M+1)$^+$. $^1$H NMR (400 MHz, DMSO) δ 10.31 (s, 1H), 9.01 (s, 1H), 8.88 (d, J=2.3 Hz, 1H), 8.33 (d, J=2.3 Hz, 1H), 7.87 (d, J=9.1 Hz, 2H), 7.35 (d, J=8.9 Hz, 2H), 5.32 (t, J=4.8 Hz, 1H), 4.27 (s, 1H), 3.56 (d, J=7.4 Hz, 1H), 3.28 (dd, J=13.2, 5.3 Hz, 2H), 2.93 (d, J=12.0 Hz, 1H), 1.92-1.85 (m, 1H), 1.80 (dt, J=15.9, 6.5 Hz, 1H).

Example 10 Preparation of (R)-6-(3-dimethylaminopyrrolidin-1-yl)-5-(isothiazol-4-yl)-N-(4-(chlorodifluoromethoxy)phenyl)nicotinamide (Compound 31)

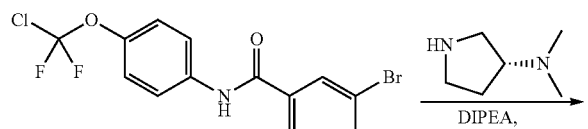

Step 1: Synthesis of (R)-6-(3-dimethylaminopyrrolidin-1-yl)-5-bromo-N-(4-(chlorodifluoromethoxy)phenyl)nicotinamide (Compound 29)

To a reaction flask were added compound 2 (0.90 g, 2.19 mmol) and (R)-3-dimethylaminopyrrolidine hydrochloride (300 mg, 2.63 mmol), 15 mL isopropyl alcohol, and DIPEA (621 mg, 4.82 mmol) were added, and the reaction was heated to 140° C. and stirred for 2 hours. After cooling to room temperature, the reaction was concentrated to remove solvent, purified by silica gel column chromatography to afford 1.06 g of a product, yield: 99%.

Step 2: Synthesis of (R)-6-(3-dimethylaminopyrrolidin-1-yl)-5-(4,4,5,5-tetramethyl-1,3,2-dioxaborolan-2-yl)-N-(4-(chlorodifluoromethoxy)phenyl)nicotinamide (Compound 30)

In a reaction flask were added compound 29 (633 mg, 1.3 mmol), bis(pinacolato)diboron (0.98 g, 3.89 mmol), palladium acetate (25 mg, 0.039 mmol), Xphos (50 mg, 0.1 mmol) and potassium phosphate (826 mg, 3.9 mmol), 20 mL anhydrous dioxane was added to dissolve the substances, and the reaction was heated to 60° C. in microwave and reacted for 4 hours. TLC detected the starting material was not completely consumed, bis(pinacolato)diboron (0.98 g, 3.89 mmol) was additionally added and reacted at 60° C. overnight. After TLC detected the reaction was complete, the reaction was concentrated, purified by silica gel column chromatography to afford 564 mg of a product, yield: 81%.

Step 3: Synthesis of (R)-6-(3-dimethylaminopyrrolidin-1-yl)-5-(isothiazol-4-yl)-N-(4-(chlorodifluoromethoxy)phenyl)nicotinamide (Compound 31)

To a reaction flask were added compound 30 (100 mg, 0.186 mmol), 4-bromoisothiazole (50 mg, 0.279 mmol), Pd(dppf)Cl$_2$ (5 mg, 0.006 mmol) and sodium carbonate (60 mg, 0.558 mmol), 5 mL glycol dimethyl ether and 0.9 mL water were added, bubbled with nitrogen gas for 10 minutes, and the reaction was heated to 100° C. in microwave and reacted for half an hour. After TLC detected the reaction was complete, the reaction was concentrated, purified by silica gel column chromatography to afford 78 mg of a product, yield: 85%. LC-MS(APCI): m/z=494.7 (M+1)$^+$. $^1$H NMR (400 MHz, CDCl$_3$) δ 8.67 (s, 1H), 8.54 (d, J=4.3 Hz, 2H), 7.96 (s, 1H), 7.91 (s, 1H), 7.67 (d, J=8.8 Hz, 2H), 7.22 (d, J=8.6 Hz, 2H), 3.43-3.34 (m, 1H), 3.34-3.21 (m, 2H), 3.18 (dd, J=17.9, 9.0 Hz, 1H), 2.67 (s, 1H), 2.23 (s, 6H), 2.05 (d, J=6.5 Hz, 1H), 1.76 (dd, J=20.3, 10.0 Hz, 1H).

Example 11 Preparation of (R)-6-(3-dimethylaminopyrrolidin-1-yl)-5-(isothiazol-5-yl)-N-(4-(chlorodifluoromethoxy)phenyl)nicotinamide (Compound 32)

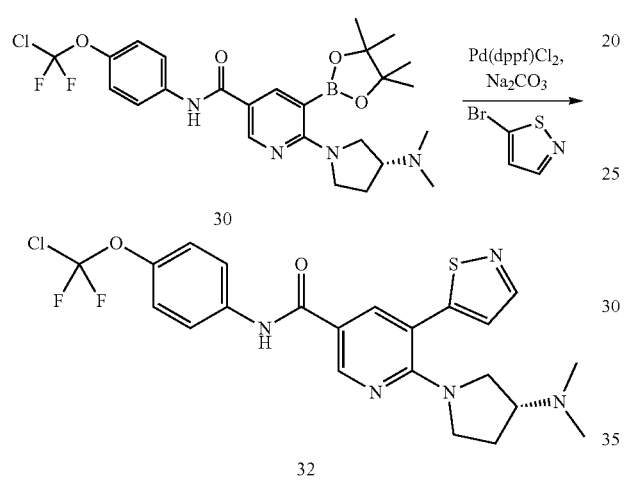

To a reaction flask were added compound 30 (100 mg, 0.186 mmol), 5-bromoisothiazole (50 mg, 0.279 mmol), Pd(dppf)Cl$_2$ (5 mg, 0.006 mmol) and sodium carbonate (60 mg, 0.558 mmol), 5 mL glycol dimethyl ether and 0.9 mL water were added, bubbled with nitrogen gas for 10 minutes, and the reaction was heated to 100° C. in microwave and reacted for half an hour. After TLC detected the reaction was complete, the reaction was concentrated, purified by silica gel column chromatography to afford 54 mg of a product, yield: 58.8%. LC-MS(APCI): m/z=494.7 (M+1)$^+$. $^1$H NMR (400 MHz, CDCl$_3$) δ 8.72 (d, J=2.3 Hz, 1H), 8.46 (d, J=1.5 Hz, 1H), 8.40 (s, 1H), 8.01 (d, J=2.3 Hz, 1H), 7.72 (d, J=9.0 Hz, 2H), 7.24-7.17 (m, 3H), 3.50 (dd, J=10.8, 7.1 Hz, 1H), 3.42 (t, J=9.6 Hz, 1H), 3.32 (dd, J=9.3, 4.4 Hz, 2H), 2.91-2.84 (m, 1H), 2.35 (s, 6H), 2.10 (dd, J=11.6, 6.0 Hz, 1H), 1.91 (dd, J=20.5, 10.4 Hz, 1H).

Example 12 Preparation of (R)-6-(3-dimethylaminopyrrolidin-1-yl)-5-(1,2,4-thiodiazol-5-yl)-N-(4-(chlorodifluoromethoxy)phenyl)nicotinamide (Compound 36)

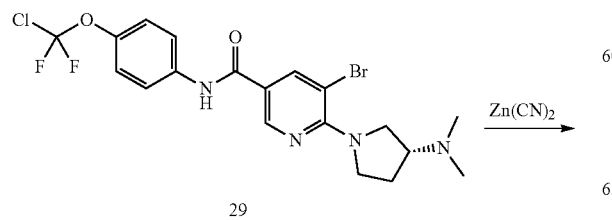

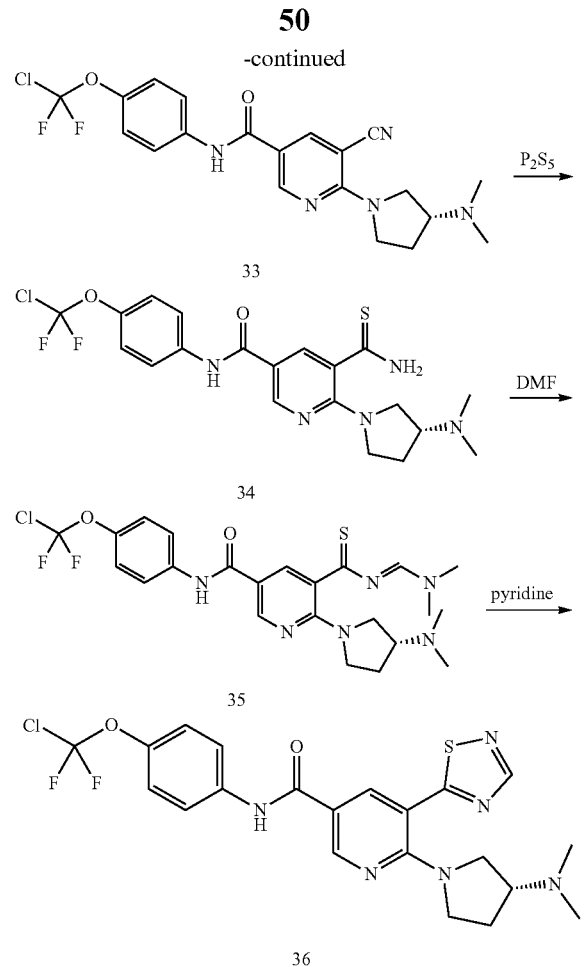

According to the same procedures as those used in the preceding Examples, the title product compound 36 was finally obtained. LC-MS(APCI): m/z=495.0 (M+1)$^+$. $^1$H NMR (400 MHz, DMSO) δ 10.34 (s, 1H), 9.02 (s, 1H), 8.88 (d, J=2.3 Hz, 1H), 8.36 (d, J=2.3 Hz, 1H), 7.87 (d, J=9.1 Hz, 2H), 7.35 (d, J=9.0 Hz, 2H). 3.50 (dd, J=10.8, 7.1 Hz, 1H), 3.42 (t, J=9.6 Hz, 1H), 3.32 (dd, J=9.3, 4.4 Hz, 2H), 2.91-2.84 (m, 1H), 2.35 (s, 6H), 2.10 (dd, J=11.6, 6.0 Hz, 1H), 1.91 (dd, J=20.5, 10.4 Hz, 1H).

Example 13 Preparation of 6-(3-hydroxy-4-fluoropyrrolidin-1-yl)-5-(isothiazol-4-yl)-N-(4-(chlorodifluoromethoxy)phenyl)nicotinamide (Compound 42)

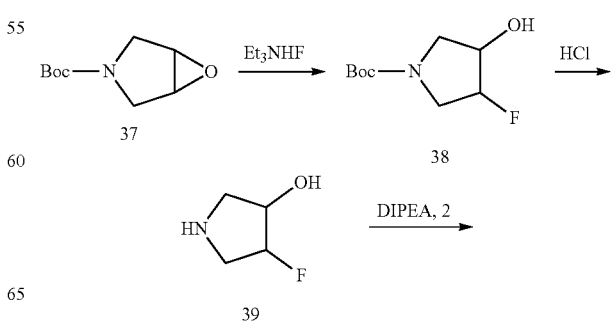

-continued

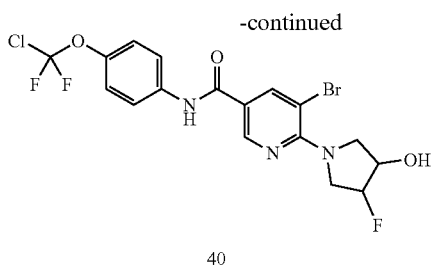

40

41

42

Step 1: Synthesis of 3-hydroxy-4-fluoro-N-tert-butoxycarbonylpyrrolidine (Compound 38)

To a reaction flask were added 3-tert-butoxycarbonyl-6-oxa-3-azabicyclo[3.1.0]hexane (1.11 g, 6.0 mmol) and triethylamine trihydrofluoride (967.3 mg, 7.2 mmol), and the reaction was heated to 100° C. and stirred overnight. After cooling to room temperature, the reaction was purified by silica gel column chromatography to afford 881 mg of a product, yield: 71.6%.

Step 2: Synthesis of 3-hydroxy-4-fluoropyrrolidine (Compound 39)

To a reaction flask were added compound 38 (881 mg, 4.29 mmol) and 4 M HCl in dioxane (27 ml, 107.4 mmol), and the reaction was stirred at room temperature for 3-4 hours. After TLC detected the reaction was complete, the reaction was concentrated to remove solvent, which was used in the next step without purification.

Step 3: Synthesis of 6-(3-hydroxy-4-fluoropyrrolidin-1-yl)-5-bromo-N-(4-(chlorodifluoromethoxy)phenyl)nicotinamide (Compound 40)

To a reaction flask were added compound 2 (883 mg, 2.15 mmol) and compound 39 (276.1 mg, 2.63 mmol), 15 mL isopropyl alcohol was added, DIPEA (610 mg, 4.73 mmol) was added, and the reaction was heated to 140° C. and stirred for 2 hours. After cooling to room temperature, the reaction was concentrated to remove solvent, purified by silica gel column chromatography to afford 896 mg of a product, yield: 87%.

Step 4: Synthesis of 6-(3-hydroxy-4-fluoropyrrolidin-1-yl)-5-(4,4,5,5-tetramethyl-1,3,2-dioxaborolan-2-yl)-N-(4-(chlorodifluoromethoxy)phenyl)nicotinamide (Compound 41)

In a reaction flask were added compound 40 (650 mg, 1.35 mmol), bis(pinacolato)diboron (1.03 g, 4.06 mmol), palladium acetate (10 mg, 0.045 mmol), Xphos (50 mg, 0.1 mmol) and potassium phosphate (861 mg, 4.06 mmol), 20 mL anhydrous dioxane was added to dissolved the substances, and the reaction was heated to 60° C. in microwave and reacted for 4 hours. TLC detected the starting material was not completely consumed, bis(pinacolato)diboron (1.03 g, 4.06 mmol) was additionally added and reacted at 60° C. overnight. After TLC detected the reaction was complete, it was concentrated, purified by silica gel column chromatography to afford 664 mg of a product, yield: 93.4%.

Step 5: Synthesis of 6-(3-hydroxy-4-fluoropyrrolidin-1-yl)-5-(isothiazol-4-yl)-N-(4-(chloro difluoromethoxy)phenyl) nicotinamide (Compound 42)

To a reaction flask were added compound 41 (100 mg, 0.19 mmol), 4-bromoisothiazole (50 mg, 0.27 mmol), Pd(dppf)Cl$_2$ (5 mg, 0.006 mmol) and sodium carbonate (60 mg, 0.558 mmol), 5 mL glycol dimethyl ether and 0.9 mL water were added, bubbled with nitrogen gas for 10 minutes, and the reaction was heated to 100° C. in microwave and reacted for half an hours. After TLC detected the reaction was complete, the reaction was concentrated, purified by silica gel column chromatography to afford 58 mg of a product, yield: 63%. LC-MS(APCI): m/z=485.3 (M+1)$^+$. $^1$H NMR (400 MHz, CDCl$_3$) δ 10.23 (s, 1H), 9.09 (s, 1H), 8.77 (d, J=2.0 Hz, 1H), 8.72 (s, 1H), 8.10 (d, J=2.0 Hz, 1H), 7.87 (d, J=9.0 Hz, 2H), 7.34 (d, J=8.7 Hz, 2H), 5.47 (d, J=3.5 Hz, 1H), 4.94 (d, J=51.5 Hz, 1H), 4.18 (s, 1H), 3.64 (ddd, J=41.8, 13.5, 3.1 Hz, 1H), 3.43-3.38 (m, 1H), 3.02 (d, J=11.9 Hz, 1H).

Example 14 Preparation of 6-(3-hydroxy-4-fluoropyrrolidin-1-yl)-5-(isothiazol-5-yl)-N-(4-(chlorodifluoromethoxy)phenyl)nicotinamide (Compound 43)

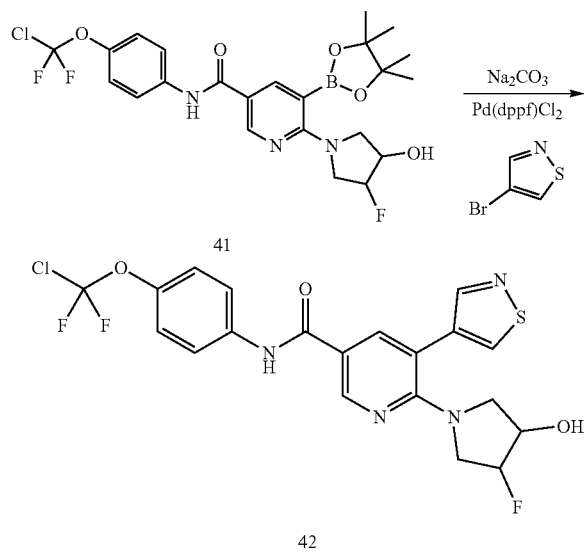

41

43

To a reaction flask were added compound 41 (100 mg, 0.19 mmol), 5-bromoisothiazole (50 mg, 0.27 mmol), Pd(dppf)Cl$_2$ (5 mg, 0.006 mmol) and sodium carbonate (60 mg, 0.558 mmol), 5 mL glycol dimethyl ether and 0.9 mL water were added, bubbled with nitrogen gas for 10 minutes, and the reaction was heated to 100° C. in microwave and reacted for half an hours. After TLC detected the reaction was complete, the reaction was concentrated, purified by silica gel column chromatography to afford 29 mg of a product, yield: 31.5%. LC-MS(APCI): m/z=485.3 (M+1)$^+$. $^1$H NMR (400 MHz, DMSO) δ 10.29 (s, 1H), 8.82 (d, J=2.3 Hz, 1H), 8.65 (d, J=1.6 Hz, 1H), 8.15 (d, J=2.3 Hz, 1H), 7.87 (d, J=9.1 Hz, 2H), 7.50 (d, J=1.6 Hz, 1H), 7.34 (d, J=9.0 Hz, 2H), 5.50 (d, J=2.8 Hz, 1H), 4.97 (d, J=52.1 Hz, 1H), 4.21 (s, 1H), 3.75 (ddd, J=41.8, 13.6, 3.3 Hz, 1H), 3.51 (d, J=12.1 Hz, 1H), 3.46-3.36 (m, 1H), 3.08 (d, J=11.9 Hz, 1H).

Example 15 Preparation of 6-(3-hydroxy-4-fluoro-pyrrolidin-1-yl)-5-(1,2,4-thiodiazol-5-yl)-N-(4-(chlorodifluoromethoxy)phenyl)nicotinamide (Compound 47)

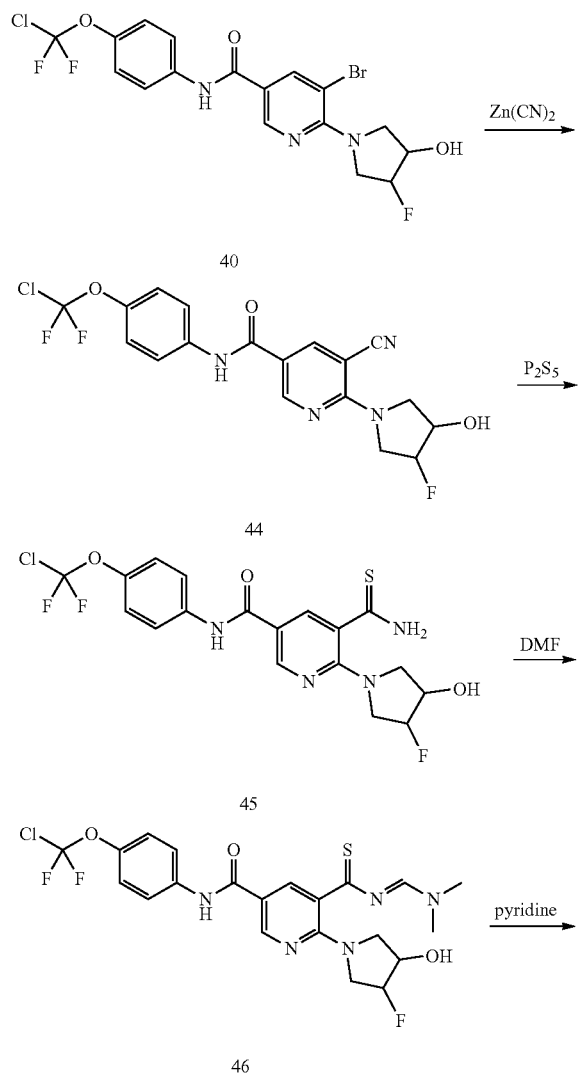

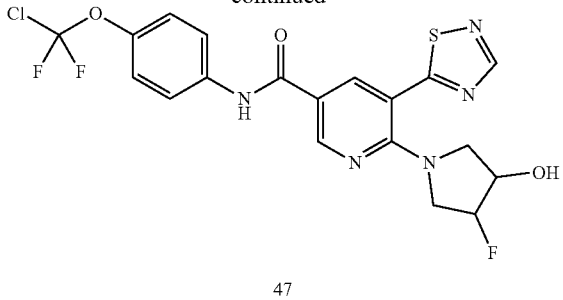

According to the same procedures as those used in the preceding Examples, the title product compound 47 was finally obtained. LC-MS(APCI): m/z=486.8 (M+1)$^+$. $^1$H NMR (400 MHz, DMSO) δ 10.35 (s, 1H), 9.04 (s, 1H), 8.90 (d, J=2.3 Hz, 1H), 8.37 (d, J=2.3 Hz, 1H), 7.86 (t, J=6.0 Hz, 2H), 7.35 (d, J=8.9 Hz, 2H), 5.54 (d, J=3.3 Hz, 1H), 5.00 (d, J=52.8 Hz, 1H), 4.25 (s, 1H), 3.91-3.77 (m, 1H), 3.61 (d, J=12.1 Hz, 1H), 3.46-3.38 (m, 1H), 3.02 (d, J=12.2 Hz, 1H).

Biological Activity Test

Example 16: Cytotoxicity experiment

The inhibitory effect of the Example compounds on the activity of Ba/F$_3$ parent cell, Ba/F$_3$ Bcr-Abl$^{T315I}$ cell was examined.

Materials and reagents: RPMI-1640 medium (GIBCO, Cat. No. A10491-01), fetal bovine serum (GIBCO, Cat. No. 10099141), antibiotics (penicillin-streptomycin), IL-3 (PeproTech), puromycin; Cell lines: Ba/F$_3$ parental cell, Ba/F$_3$ Bcr-Abl$^{T315I}$ (purchased from American Standard Biological Collection Center, ATCC), live cell assay kit CellTiter-Glo4 (Promega, Cat. No. G7572), 96-well cell culture plate with black wall and transparent flat bottom (Corning, Cat. No. 3340).

Experimental Procedures

1. Preparation of cell plate: Ba/F$_3$ parental cells, Ba/F$_3$ Bcr-Abl$^{T315I}$ cells were seeded in 96-well plates, and 8 ng/ml IL-3 was added to Ba/F$_3$ parental cells. The cell plates were placed in carbon dioxide culture and incubated overnight.

2. Preparation of test compounds: The test compounds were dissolved in DMSO and subjected to a 3.16-fold gradient dilution in triplicate, 9 concentrations were obtained, starting from the concentration of 10 μM.

3. Treatment of Cells with compounds: Compounds at various concentrations were transferred to cell plates. The cell plates were incubated in a carbon dioxide incubator for 3 days.

4. Detection: CellTiter-Glo4 reagent was added to the cell plates, which were incubated for 30 minutes at room temperature to stabilize the luminescence signal. Readings were performed using a PerkinElmer Envision multi-label analyzer.

The results of in vitro inhibition of cell proliferation in the examples are summarized in Table 1 below, wherein A represents IC$_{50}$≤100 nM, B represents 100 nM<IC$_{50}$≤500 nM, C represents 500 nM<IC$_{50}$≤1000 nM, and D represents IC$_{50}$>1000 nM.

TABLE 1 cytotoxic effects of the Example compounds

| Example No. | Ba/F$_3$ parent cells IC$_{50}$ | Ba/F$_3$ Bcr-Abl$^{T315I}$ IC$_{50}$ |
|---|---|---|
| Example 1 | D | B |
| Example 2 | D | A |
| Example 3 | D | A |
| Example 4 | D | C |
| Example 5 | D | D |
| Example 6 | D | B |

The experimental results show that, the compounds disclosed herein exhibit relatively low inhibitory activity against Ba/F$_3$ cells that are related to drug side effects (IC$_{50}$ greater than 1000 nM), and exhibit excellent inhibitory activity against Ba/F$_3$ Bcr-Abl$^{T315I}$ mutant cells (the optimal IC$_{50}$≤100 nM). Therefore, the compounds disclosed herein can be used as Bcr-Abl inhibitors for use in the treatment of patients with tumor that is resistant to existing tyrosine kinase inhibitor (TKI) treatment, with have good prospects, such as chronic, blast, and accelerated phases of chronic myeloid leukemia (CML) patients and chronic myeloid leukemia and acute lymphoblastic leukemia patients with Philadelphia chromosome-positive (Ph$^+$).

Furthermore, the compounds disclosed herein also have an excellent therapeutic index (obtained by dividing the IC$_{50}$ of the Ba/F$_3$ parent cells by the IC$_{50}$ of Ba/F$_3$ Bcr-Abl$^{T315I}$), for example, the compound of Example 2 has a therapeutic index greater than 180, and the compound of Example 3 has a therapeutic index greater than 90.

Example 17: Pharmacokinetic Experiment in Rats

6 Male Sprague-Dawley rats, 7-8 weeks old, weighted 210 g, divided into 2 groups with 3 rats in each group, were intravenously (2 mg/kg) or orally (20 mg/kg) given a single dose of compound, and differences in pharmacokinetics of the rats were compared.

Rats were fed with a standard diet and water. Fasting began 16 hours before the test. The drugs were dissolved in PEG400 and dimethyl sulfoxide. Blood was collected from the eyelids at a time point of 0.083 hour, 0.25 hour, 0.5 hour, 1 hour, 2 hours, 4 hours, 6 hours, 8 hours, 12 hours, and 24 hours after administration.

Rats were briefly anesthetized after inhalation of ether, and 300 μL of blood samples were collected from the eyelids to test tubes. There was 30 μL of 1% heparin salt solution in the test tube. The tubes were dried overnight at 60° C. before use. After the blood sample was collected at the last time point, rats were anesthetized with ether and sacrificed.

Immediately after the collection, blood samples were sufficiently mixed by gently inverting the tube at least 5 times, and were placed on ice. Blood samples were centrifuged at 5000 rpm for 5 minutes at 4° C. to separate plasma from red blood cells. 100 μL of the plasma was pipetted into a clean plastic centrifuge tube, marking the name of the compound and collecting time. Plasma was stored at −80° C. prior to analysis. The concentration of the compounds disclosed herein in plasma was determined by LC-MS/MS. Pharmacokinetic parameters were calculated based on drug concentrations in plasma of each animal at different time points.

In this experiment, ABL-001 was used as a positive control, and the experimental results are shown in Table 2 below.

TABLE 2

PK parameters of Example compounds in rats

| PK parameters | ABL-001 | | Example 2 | |
|---|---|---|---|---|
| | IV | PO | IV | PO |
| C$_{max}$ (ng/mL) | 10081.3 | 1766.2 | 5282.5 | 2582.0 |
| AUC$_{last}$ (h*ng/mL) | 6900.6 | 13706.4 | 5450.5 | 21093.8 |
| MRT$_{INF\ pred}$ (h) | 1.12 | 5.52 | 1.17 | 5.13 |
| Vz$_{pred}$ (L/kg) | 0.54 | 5.14 | 0.57 | 2.56 |
| Cl$_{pred}$ (L/kg) | 0.30 | 1.66 | 0.37 | 0.96 |
| F(%) | 19.86 | | 38.70 | |

The experimental results indicate that the compounds disclosed herein have better pharmacokinetic properties. For example, after orally administering the compound of Example 2 and ABL-001 to rats, the compound of Example 2 was found to have better metabolic parameters—maximum plasma exposure (C$_{max}$), plasma exposure (AUC$_{last}$), and oral availability (F %).

Example 18: Pharmacodynamic Evaluation of BA/F3 (BCR-ABL$^{T315I}$) in Subcutaneous Tumor Model Experimental Animals:

32 NOD/SCID mice, female, 7-8 weeks old (age at tumor cell inoculation), average body weight 21.8 g, were purchased from Beijing Huafukang Bioscience Co., Inc, animal certificate number: 11401300068166. Feeding environment: SPF level.

Environmental Conditions of the Breeding Room for Experimental Animals:

The experimental animals were kept in separate ventilated boxes with constant temperature and humidity, wherein the temperature of the breeding room was 22.3-24.5° C., the humidity was 51-58%, the ventilation is 10-20 times/hour, and 12 h/12 h day and night; rat full-price pellet feed, that was sterilized with cobalt 60 radiation, was continuous supplied and freely accessible without limitation, and drinking tap water (used after high-pressure steam sterilization), was continuous supplied in water bottle and freely accessible. The rat boxes are polysulfone mouse boxes, which were used after autoclaving. The specification of the boxes is 325 mm×210 mm×180 mm, the bedding is autoclaved corn cob, 4 animals per box. The IACUC approval number, experiment number, experiment starting time, project leader, experimenter, animal source, group, animal number, etc. were indicated on the cage; and experimental animals were marked with ear tags.

Methods:

Each NOD/SCID mouse was subcutaneously inoculated with 5×10$^6$ BA/F3(BCR-ABL$^{T315I}$) cells in the right dorsal area, wherein the cells were resuspended in PBS (0.1 ml/mouse), to establish a subcutaneous tumor model. The tests were divided into vehicle control group, positive control ABL001 15 mg/kg group, the compound of Example 2 15 mg/kg group; 6 mice in each group. The mice were dosed twice a day, vehicle control group was administered for 15 days, positive control ABL001 15 mg/kg was administered for 19 days, and the compound of Example 2 15 mg/kg group was administered for 19 days. The efficacy was evaluated according to the relative tumor growth inhibition rate (TGI), and the safety evaluation was performed according to the body weight changes and deaths of the animals.

The experimental protocols for animal experiment disclosed herein were reviewed and approved by the CrownBio IACUC committee. During the experiment, the procedures of the animal experiment were carried out according to the requirements of AAALAC. After tumor inoculation, the effects of tumor growth and treatment on normal animal behavior were routinely monitored, including experimental animal activity, feeding and drinking, weight gain or loss, eye, hair and other abnormalities. Abnormal clinical symptoms observed during the experiment were recorded in the raw data. Mice body weight and tumor size were measured and recorded three times per week during the experiment. The mice were weighed before each administration and administered according to the weight thereof.

Relative Tumor Growth Inhibition Rate TGI (%):

TGI %=(1−T/C)×100%. T/C % is the relative tumor proliferation rate, that is, the percentage of tumor volume or tumor weight of the treatment group and the control group at a certain time point. T and C are the relative tumor volume (RTV) or tumor weight (TW) of the treatment group and the control group at a specific time point, respectively.

Statistical Analysis:

All experimental results were expressed as mean±standard error (x̄±s), and the significant difference of the tumor volume at 12 days after grouping between the control group and each treatment group was evaluated with one-way ANOVA, and significant difference of the tumor volume between the control group and each treatment group or between each treatment group was evaluated using Games-Howell (heterogeneity of variance), p<0.05 was considered to be significant.

Experimental Results

In the BA/F$_3$ (BCR-ABL$^{T315I}$) subcutaneous tumor model, the compounds disclosed herein have better anti-tumor effects and better safety. For example, the relative tumor growth inhibition rate (TGI) of the compound of Example 2 was at least 20% higher than that of ABL-001; during the experiment, the average body weight in the ABL-001 group decreased by 5%, while in the compound of Example 2 group the average body weight of the mice increased, and it can be concluded from the changes in body weight of the mice that: the compound of Example 2 was safer than ABL-001.

It is to be understood that the examples are merely illustrative of the invention and are not intended to limit the scope of the invention, and the experimental methods in which the specific conditions are not indicated, are carried out generally in accordance with conventional conditions, or in accordance with the conditions suggested by the manufacturer. Parts and percentages are parts by weight and percentage by weight unless otherwise stated.

The above is a further detailed description of the present disclosure in connection with the specific preferred embodiments, and the specific embodiments of the present disclosure are not limited to the description. It will be apparent to those skilled in the art that the present disclosure may be practiced by making various simple deduction and replacement, without departing from the spirit and scope of the invention.

The invention claimed is:

1. A compound, or a pharmaceutically acceptable salt, or a stereoisomer thereof, wherein the said compound is selected from:

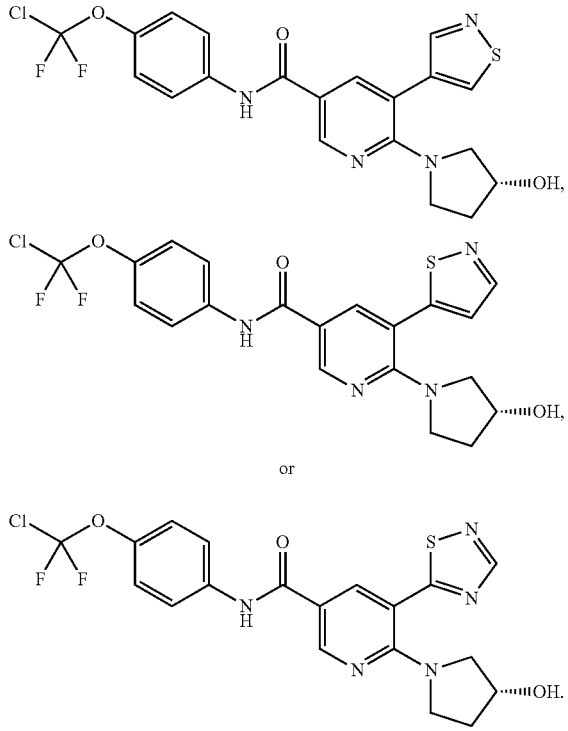

2. The compound according to claim 1, which is

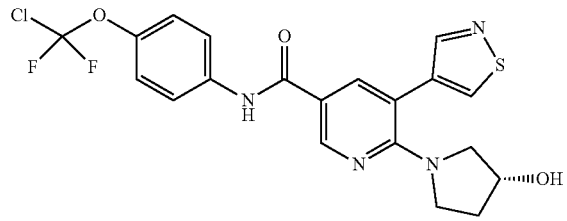

or a pharmaceutically acceptable salt thereof.

3. The compound according to claim 1, which is

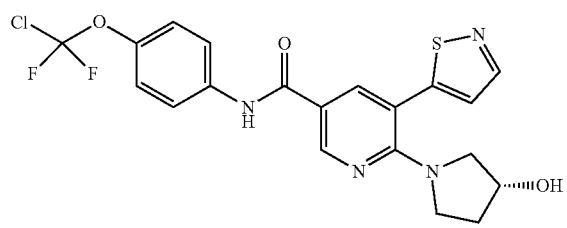 [SMILES: O=C(Nc1ccc(OC(F)(F)Cl)cc1)c1cnc(N2CC[C@@H](O)C2)c(-c2ccns2)c1]

or a pharmaceutically acceptable salt thereof.

4. The compound according to claim 1, which is

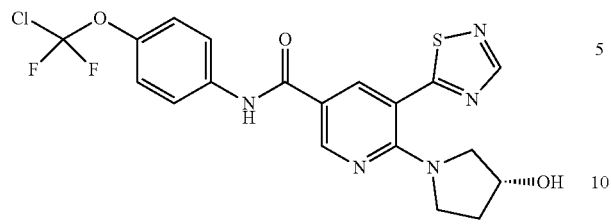

or a pharmaceutically acceptable salt thereof.

5. A pharmaceutical composition, comprising:
the compound according to claim 1 or a pharmaceutically acceptable salt, or a stereoisomer thereof, and pharmaceutically acceptable excipients.

6. A pharmaceutical composition, comprising:
the compound according to claim 2 or a pharmaceutically acceptable salt thereof, and pharmaceutically acceptable excipients.

7. A pharmaceutical composition, comprising:
the compound according to claim 3 or a pharmaceutically acceptable salt thereof, and pharmaceutically acceptable excipients.

8. A pharmaceutical composition, comprising:
the compound according to claim 4 or a pharmaceutically acceptable salt thereof, and pharmaceutically acceptable excipients.

* * * * *